United States Patent
Shim et al.

(10) Patent No.: US 9,962,128 B2
(45) Date of Patent: May 8, 2018

(54) WATCH TYPE TERMINAL AND METHOD FOR CONTROLLING THE SAME

(71) Applicant: LG ELECTRONICS INC., Seoul (KR)

(72) Inventors: Hongjo Shim, Seoul (KR); Yoonwoo Lee, Seoul (KR); Hyunwoo Kim, Seoul (KR); Gukchan Lim, Seoul (KR); Seonghyok Kim, Seoul (KR); Mihyun Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 254 days.

(21) Appl. No.: 14/843,601

(22) Filed: Sep. 2, 2015

(65) Prior Publication Data

US 2016/0354042 A1     Dec. 8, 2016

(30) Foreign Application Priority Data

Jun. 2, 2015    (KR) .......................... 10-2015-0078087

(51) Int. Cl.
    *A61B 5/02*          (2006.01)
    *A61B 5/00*          (2006.01)
    (Continued)

(52) U.S. Cl.
    CPC .............. *A61B 5/742* (2013.01); *A61B 5/024* (2013.01); *A61B 5/681* (2013.01); *G06F 21/32* (2013.01); *G06F 21/35* (2013.01)

(58) Field of Classification Search
    CPC ......... A61B 5/024; A61B 5/742; A61B 5/681; G06F 21/32; G06F 21/35
    See application file for complete search history.

(56) References Cited

U.S. PATENT DOCUMENTS

| 2004/0051642 A1 | 3/2004 | Choi |
| 2006/0028429 A1* | 2/2006 | Kanevsky ............... G06F 3/017 345/156 |

(Continued)

FOREIGN PATENT DOCUMENTS

| EP | 2733579 | 5/2014 |
| JP | 2002261901 | 9/2002 |
| KR | 20140126027 | 10/2014 |

OTHER PUBLICATIONS

PCT International Application No. PCT/KR2015/008402, Written Opinion of the International Searching Authority dated Mar. 2, 2016, 12 pages.

(Continued)

*Primary Examiner* — Navin Natnithithadha
*Assistant Examiner* — Eric Messersmith
(74) *Attorney, Agent, or Firm* — Lee, Hong, Degerman, Kang & Waimey PC

(57) ABSTRACT

The present invention relates to a wearable terminal includes a display comprising a front side and a rear side, a first sensing unit configured to sense a biometric characteristic and disposed at the rear side of the display to be proximate to or contact a user's body, a second sensing unit configured to sense a movement of the terminal; and controller configured to execute a different function based on the movement of the terminal when a sensing strength of the biometric characteristic via the first sensing unit is greater than a threshold strength level, wherein the sensing strength is varied based on a portion of the user's body which the first sensing unit is proximate to or is in contact with.

19 Claims, 30 Drawing Sheets

(51) Int. Cl.
    *G06F 21/32*     (2013.01)
    *G06F 21/35*     (2013.01)
    *A61B 5/024*     (2006.01)

(56) References Cited

U.S. PATENT DOCUMENTS

| | | | |
|---|---|---|---|
| 2007/0167844 A1* | 7/2007 | Asada | A61B 5/022 |
| | | | 600/485 |
| 2014/0058935 A1 | 2/2014 | Mijares | |
| 2014/0085050 A1 | 3/2014 | Luna | |
| 2014/0164611 A1* | 6/2014 | Molettiere | A61B 5/6838 |
| | | | 709/224 |
| 2014/0278220 A1 | 9/2014 | Yuen | |
| 2015/0085621 A1 | 3/2015 | Hong et al. | |
| 2015/0135310 A1* | 5/2015 | Lee | A61B 5/681 |
| | | | 726/20 |
| 2016/0213324 A1* | 7/2016 | Gil | A61B 5/7278 |

OTHER PUBLICATIONS

European Patent Office Application Serial No. 15002475.0, Search Report dated Mar. 16, 2016, 6 pages.

\* cited by examiner

MESSAGE RECEPTION

⇩ MESSAGE RECEPTION

WATCH TYPE TERMINAL AND METHOD FOR CONTROLLING THE SAME

CROSS-REFERENCE TO RELATED APPLICATION

Pursuant to 35 U.S.C. § 119(a), this application claims the benefit of earlier filing date and right of priority to Korean Application No. 10-2015-0078087, filed on Jun. 2, 2015, the contents of which is incorporated by reference herein in its entirety.

BACKGROUND OF THE DISCLOSURE

1. Field of the Disclosure

This specification relates to a watch type terminal capable of providing various functions through biometric recognition, and a method for controlling the same.

2. Background of the Disclosure

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

As it becomes multifunctional, a mobile terminal can be allowed to capture still images or moving images, play music or video files, play games, receive broadcast and the like, so as to be implemented as an integrated multimedia player.

Efforts are ongoing to support and increase the functionality of mobile terminals. Such efforts include software and hardware improvements, as well as changes and improvements in the structural components.

In recent time, such mobile terminal is developed into a wearable device in the form of being wearable on a part of a user's body. In terms of being wearable on the part of the user's body, the wearable device may have a form which is advantageous for measuring user's biometric data (biometric information or bio-information), compared with the conventional mobile terminal. For example, a watch type terminal which is produced to be wearable on a wrist can more conveniently sense (or detect) such biometric data than the conventional mobile terminal.

Accordingly, requirements for sensing (detecting, recognizing) user's biometric data using a wearable device and performing various functions according to the sensed biometric data are gradually increasing.

SUMMARY OF THE DISCLOSURE

Therefore, an aspect of the detailed description is to provide various functions using a characteristic of biometric data in a watch type terminal sensing such biometric data.

Another aspect of the detailed description is to more reinforce security of a watch type terminal according to a characteristic of biometric data.

To achieve these and other advantages and in accordance with the purpose of this specification, as embodied and broadly described herein, there is provided a watch type terminal including a display unit having front and rear surfaces, a first sensing unit disposed on a rear surface of the display unit to be proximate to or come in contact with at least a part of a user's body, and configured to sense biometric data for the user, a second sensing unit configured to sense a motion of the watch type terminal, and a controller configured to execute a different function based on the motion of the watch type terminal when sensing strength of the user's biometric data is more than a preset strength level, wherein the sensing strength of the user's biometric data varies according to a portion of the user's body which the first sensing unit is proximate to or comes in contact with.

In one embodiment disclosed herein, the motion of the watch type terminal may be a rotary motion in one of a first direction or a second direction centering on the user's wrist as a rotation shaft. The controller may execute a first mode of providing functions using personal information when the watch type terminal is rotated in the first direction, and execute a second mode of providing functions without using the personal information when the watch type terminal is rotated in the second direction.

In one embodiment disclosed herein, the user's biometric data may include at least one of a heart rate and pulse strength associated with the user.

In one embodiment disclosed herein, the controller may execute a first mode of deciding activation or deactivation of the display unit according to the motion of the watch type terminal when the sensing strength of the user's biometric data is lower than the preset strength level. The controller may execute a second mode of not deciding activation or deactivation of the display unit according to the motion of the watch type terminal when the sensing strength of the user's biometric data is more than the preset strength level.

In one embodiment disclosed herein, the controller may maintain the display unit in a deactivated state even though the motion of the watch type terminal is sensed through the second sensing unit when the second mode is executed.

In one embodiment disclosed herein, the controller may switch the display unit from a deactivated state into an activated state, in response to a reception of a user's request while the second mode is executed.

In one embodiment disclosed herein, the controller may execute a driving mode function of providing functions associated with driving of a vehicle, when the sensing strength of the user's biometric data is more than the preset strength level and the motion of the watch type terminal is a preset motion.

In one embodiment disclosed herein, the controller may calculate driving safety of the vehicle using the user's biometric data, and output notification information when the driving safety of the vehicle is less than a preset value.

In one embodiment disclosed herein, the controller may activate at least one sensor for sensing information related to the driving of the vehicle, when the driving mode function is executed.

In one embodiment disclosed herein, the controller may restrict an output of notification information, which is generated from at least one application installed in the watch type terminal, when the driving mode function is executed.

In one embodiment disclosed herein, the controller may determine a user's motion through the second sensing unit. The controller may output notification information to move the second sensing unit to a specific position of the user's body when the user's motion corresponds to a preset motion.

The controller may execute an exercise mode of measuring the user's motion when the sensing strength of the user' biometric data is more than the preset strength level after the output of the notification information.

In one embodiment disclosed herein, the notification information may be information for notifying that the second sensing unit has to come in contact with or be proximate to the specific position of the user's body.

In one embodiment disclosed herein, the watch type terminal may further include a payment unit configured to perform a payment function. The controller may execute a mode of performing the payment function by activating the payment unit when the sensing strength of the user' biometric data is more than the preset strength level.

In one embodiment disclosed herein, the controller may decide a payment limit of the payment function on the basis of the sensing strength of the user's biometric data.

In one embodiment disclosed herein, the controller may decide a notification information output method on the basis of the motion of the watch type terminal when it is sensed that the user is in a vehicle and the sensing strength of the user's biometric data is more than the preset strength level.

To achieve these and other advantages and in accordance with the purpose of this specification, as embodied and broadly described herein, there is provided a method for controlling a watch type terminal configured to be wearable on a user's wrist, the method including sensing a motion of the watch type terminal, sensing biometric data for the user, and executing a different function on the basis of the motion of the watch type terminal when sensing strength of the user's biometric data is more than a preset strength level, wherein the sensing strength of the user's biometric data varies according to a portion of the user's wrist which the watch type terminal is proximate to or comes in contact with.

In one embodiment disclosed herein, the motion of the watch type terminal may be a rotary motion in one of a first direction or a second direction centering on the user's wrist as a rotation shaft.

In one embodiment disclosed herein, the executing of the different function may include executing a first mode of providing functions associated with privacy when the motion of the watch type terminal is the rotary motion in the first direction, and executing a second mode of providing functions associated with the user's motion when the motion of the watch type terminal is the rotary motion in the second direction.

In one embodiment disclosed herein, the executing of the different function may include deciding a notification information output method notifying an event generated from at least one application, installed in the watch type terminal, based on the motion of the watch type terminal when the sensing strength of the user's biometric data is more than the preset strength level.

Further scope of applicability of the present application will become more apparent from the detailed description given hereinafter. However, it should be understood that the detailed description and specific examples, while indicating preferred embodiments of the disclosure, are given by way of illustration only, since various changes and modifications within the spirit and scope of the disclosure will become apparent to those skilled in the art from the detailed description.

BRIEF DESCRIPTION OF THE DRAWINGS

The accompanying drawings, which are included to provide a further understanding of the disclosure and are incorporated in and constitute a part of this specification, illustrate exemplary embodiments and together with the description serve to explain the principles of the disclosure.

In the drawings.

DETAILED DESCRIPTION OF THE DISCLOSURE

Figure 1A:
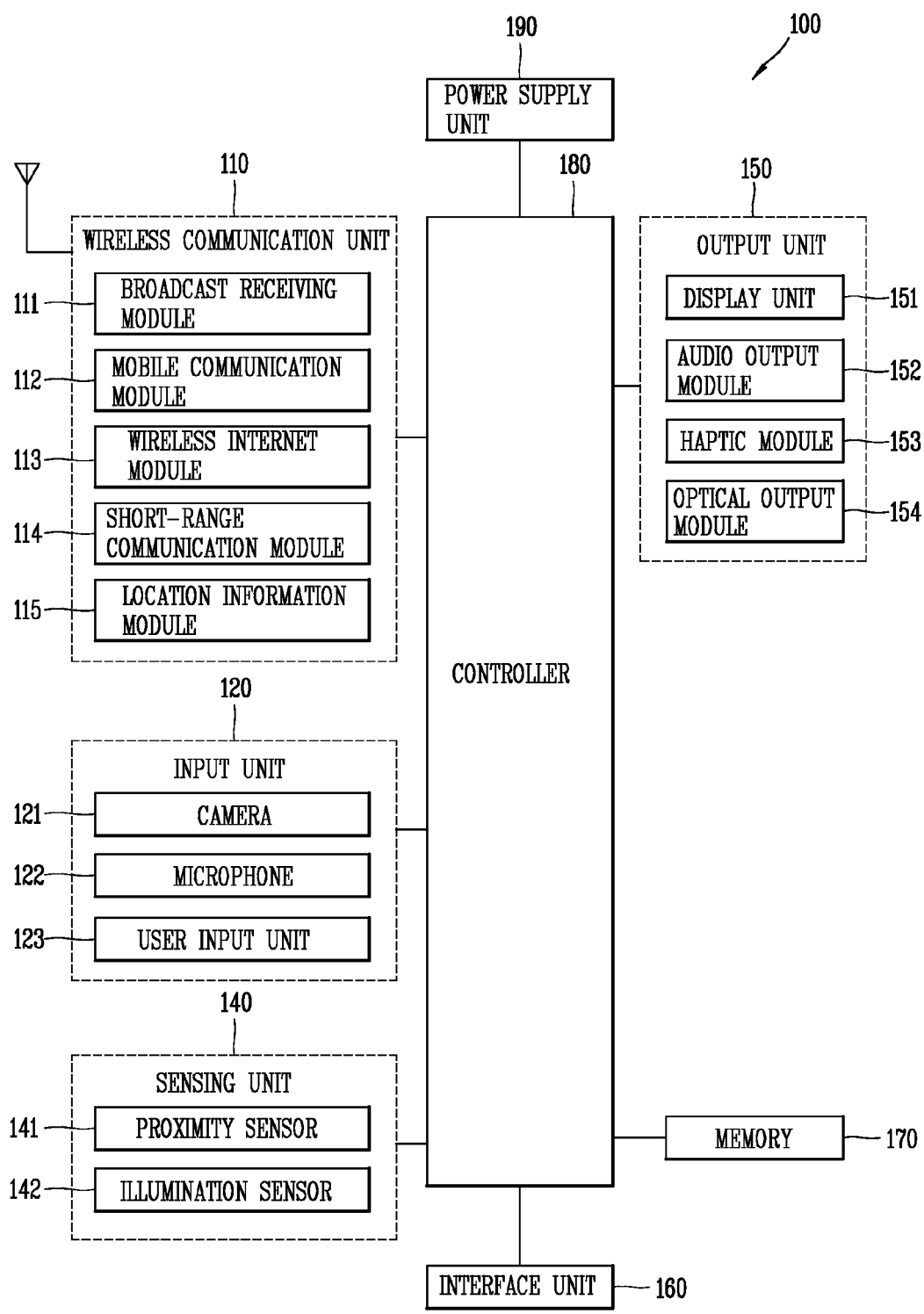
FIG. 1A is a block diagram of a mobile terminal in accordance with the present disclosure.

Description will now be given in detail according to exemplary embodiments disclosed herein, with reference to the accompanying drawings. For the sake of brief description with reference to the drawings, the same or equivalent components may be provided with the same or similar reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context.

Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

FIG. 1A is a block diagram of a mobile terminal in accordance with the present disclosure.

The mobile terminal 100 may be shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

In more detail, the wireless communication unit 110 may typically include one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 may typically include one or more modules which connect the mobile terminal 100 to one or more networks.

The wireless communication unit 110 may include one or more of a broadcast receiving module 111, a mobile communication module 112, a wireless Internet module 113, a short-range communication module 114, and a location information module 115.

The input unit 120 may include a camera 121 or an image input unit for obtaining images or video, a microphone 122, which is one type of audio input device for inputting an audio signal, and a user input unit 123 (for example, a touch key, a mechanical key, and the like) for allowing a user to input information. Data (for example, audio, video, image, and the like) may be obtained by the input unit 120 and may be analyzed and processed according to user commands.

The sensing unit 140 may typically be implemented using one or more sensors configured to sense internal information of the mobile terminal, the surrounding environment of the mobile terminal, user information, and the like. For example, the sensing unit 140 may include at least one of a proximity sensor 141, an illumination sensor 142, a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like). The mobile terminal disclosed herein may be configured to utilize information obtained from one or more sensors of the sensing unit 140, and combinations thereof.

The output unit 150 may typically be configured to output various types of information, such as audio, video, tactile output, and the like. The output unit 150 may be shown having at least one of a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the aforementioned various components, or activating application programs stored in the memory 170.

Also, the controller 180 controls some or all of the components illustrated in FIG. 1A according to the execution of an application program that have been stored in the memory 170. In addition, the controller 180 may control at least two of those components included in the mobile terminal to activate the application program.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

At least part of the components may cooperatively operate to implement an operation, a control or a control method of a mobile terminal according to various embodiments disclosed herein. Also, the operation, the control or the control method of the mobile terminal may be implemented on the mobile terminal by an activation of at least one application program stored in the memory 170.

Hereinafter, description will be given in more detail of the aforementioned components with reference to FIG. 1A, prior to describing various embodiments implemented through the mobile terminal 100.

First, regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), Wideband CDMA (WCDMA), High Speed Downlink Packet access (HSDPA), High Speed Uplink Packet Access (HSUPA), Long Term Evolution (LTE), LTE-advanced (LTE-A) and the like).

Examples of the wireless signals include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), High Speed Uplink Packet Access (HSUPA), Long Term Evolution (LTE), LTE-advanced (LTE-A) and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LET-A, and the like, as part of a mobile communication network, the wireless Internet module 113 performs such wireless Internet access.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

Here, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of at least part of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position (or current position) of the mobile terminal. As an example, the location information module 115 includes a Global Position System (GPS) module, a Wi-Fi module, or both. For example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module. If desired, the location information module 115 may alternatively or additionally function with any of the other modules of the wireless communication unit 110 to obtain data related to the position of the mobile terminal. The location information module 115 is a module used for acquiring the position (or the current position) and may not be limited to a module for directly calculating or acquiring the position of the mobile terminal.

The input unit 120 may be configured to permit various types of inputs to the mobile terminal 120. Examples of such inputs include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. Meanwhile, the cameras 121 may be arranged in a matrix configuration to permit a plurality of images having various angles or focal points to be input to the mobile terminal 100. Also, the cameras 121 may be located in a stereoscopic arrangement to acquire left and right images for implementing a stereoscopic image.

The microphone 122 processes an external audio signal into electric audio (sound) data. The processed audio data can be processed in various manners according to a function being executed in the mobile terminal 100. If desired, the microphone 122 may include assorted noise removing algorithms to remove unwanted noise generated in the course of receiving the external audio signal.

The user input unit 123 is a component that permits input by a user. Such user input may enable the controller 180 to control operation of the mobile terminal 100. The user input unit 123 may include one or more of a mechanical input element (for example, a mechanical key, a button located on a front and/or rear surface or a side surface of the mobile terminal 100, a dome switch, a jog wheel, a jog switch, and the like), or a touch-sensitive input element, among others. As one example, the touch-sensitive input element may be a virtual key, a soft key or a visual key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like, and generate a corresponding sensing signal. The controller 180 generally cooperates with the sending unit 140 to control operation of the mobile terminal 100 or execute data processing, a function or an operation associated with an application program installed in the mobile terminal based on the sensing signal. The sensing unit 140 may be implemented using any of a variety of sensors, some of which will now be described in more detail.

The proximity sensor 141 refers to a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like). In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data (or information) according to whether a touch with respect to a point on the touch screen is either a proximity touch or a contact touch.

A touch sensor can sense a touch (or a touch input) applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

Meanwhile, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121, which has been depicted as a component of the input unit 120, typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

Also, the display unit 151 may be implemented as a stereoscopic display unit for displaying stereoscopic images.

A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a flash memory type, a hard disk type, a solid state disk (SSD) type, a silicon disk drive (SDD) type, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control operations relating to application programs and the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

In accordance with still further embodiments, a mobile terminal may be configured as a device which is wearable on a human body. Such devices go beyond the usual technique of a user grasping the mobile terminal using their hand. Examples of the wearable device include a smart watch, a smart glass, a head mounted display (HMD), and the like.

A typical wearable device can exchange data with (or cooperate with) another mobile terminal 100. In such a device, the wearable device generally has functionality that is less than the cooperating mobile terminal. For instance, the short-range communication module 114 of a mobile terminal 100 may sense or recognize a wearable device that is near-enough to communicate with the mobile terminal. In addition, when the sensed wearable device is a device which is authenticated to communicate with the mobile terminal 100, the controller 180 may transmit data processed in the mobile terminal 100 to the wearable device via the short-range communication module 114, for example. Hence, a user of the wearable device can use the data processed in the mobile terminal 100 on the wearable device. For example, when a call is received in the mobile terminal 100, the user can answer the call using the wearable device. Also, when a message is received in the mobile terminal 100, the user can check the received message using the wearable device.

Figure 1B:
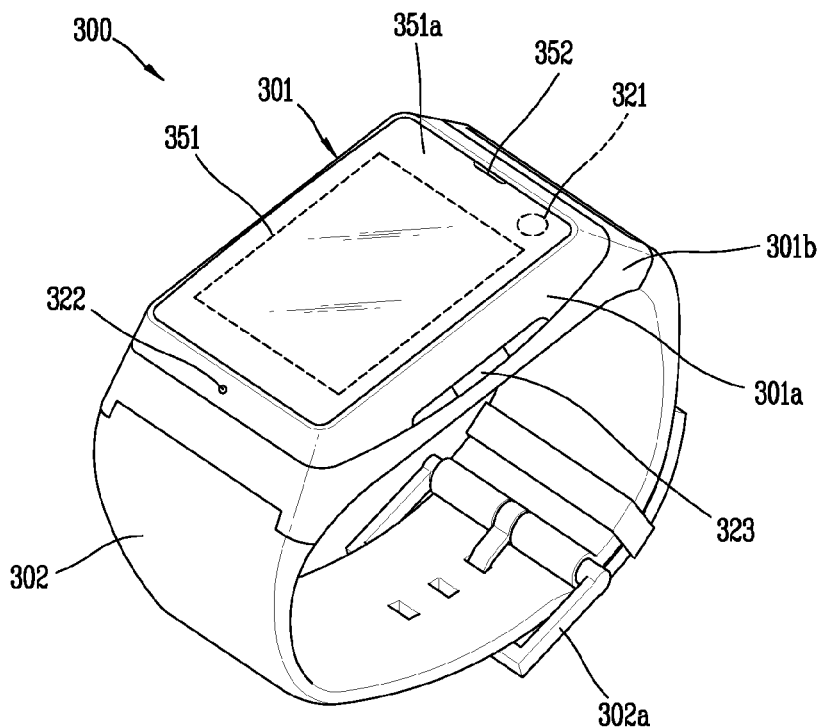
FIG. 1B is a perspective view of a watch type mobile terminal in accordance with another one embodiment of the present invention.

FIG. 1B is a perspective view illustrating one example of a watch type mobile terminal 300 in accordance with another exemplary embodiment.

As illustrated in FIG. 1B, the watch type mobile terminal 300 includes a main body 301 with a display unit 351 and a band 302 connected to the main body 301 to be wearable on a wrist. In general, mobile terminal 300 may be configured to include features that are the same or similar to that of mobile terminal 100 of FIG. 1A.

The main body 301 may include a case having a certain appearance. As illustrated, the case may include a first case 301a and a second case 301b cooperatively defining an inner space for accommodating various electronic components. Other configurations are possible. For instance, a single case may alternatively be implemented, with such a case being configured to define the inner space, thereby implementing a mobile terminal 300 with a uni-body.

The watch type mobile terminal 300 can perform wireless communication, and an antenna for the wireless communication can be installed in the main body 301. The antenna may extend its function using the case. For example, a case including a conductive material may be electrically connected to the antenna to extend a ground area or a radiation area.

The display unit 351 is shown located at the front side of the main body 301 so that displayed information is viewable to a user. In some embodiments, the display unit 351 includes a touch sensor so that the display unit can function as a touch screen. As illustrated, window 351a is positioned on the first case 301a to form a front surface of the terminal body together with the first case 301a.

The illustrated embodiment includes audio output module 352, a camera 321, a microphone 322, and a user input unit 323 positioned on the main body 301. When the display unit 351 is implemented as a touch screen, the user input unit 323 may be omitted and accordingly additional function keys may be minimized or eliminated.

The band 302 is commonly worn on the user's wrist and may be made of a flexible material for facilitating wearing of the device. As one example, the band 302 may be made of fur, rubber, silicon, synthetic resin, or the like. The band 302 may also be configured to be detachable from the main body 301. Accordingly, the band 302 may be replaceable with various types of bands according to a user's preference.

In one configuration, the band 302 may be used for extending the performance of the antenna. For example, the band may include therein a ground extending portion (not shown) electrically connected to the antenna to extend a ground area.

The band 302 may include fastener 302a. The fastener 302a may be implemented into a buckle type, a snap-fit hook structure, a Velcro® type, or the like, and include a flexible section or material. The drawing illustrates an example that the fastener 302a is implemented using a buckle.

As previously described with regard to FIG. 1A, the mobile terminal may be configured to include short-range communication techniques such as Bluetooth™, Radio Frequency Identification (RFID), Infrared Data Association (IrDA), Ultra Wideband (UWB), ZigBee, Near Field Communication (NFC), Wireless USB (Wireless Universal Serial Bus), and the like.

A typical NFC module provided at the mobile terminal supports short-range wireless communication, which is a non-contactable type of communication between mobile terminals and generally occurs within about 10 cm. The NFC module may operate in one of a card mode, a reader mode, or a P2P mode. The mobile terminal 100 may further include a security module for storing card information, in order to operate the NFC module in a card mode. The security module may be a physical medium such as Universal Integrated Circuit Card (UICC) (e.g., a Subscriber Identification Module (SIM) or Universal SIM (USIM)), a secure micro SD and a sticker, or a logical medium (e.g., embedded Secure Element (SE)) embedded in the mobile terminal. Single Wire Protocol (SWP)-based data exchange may be performed between the NFC module and the security module.

In a case where the NFC module operates in a card mode, the mobile terminal may transmit card information on a general IC card to the outside. More specifically, if a mobile terminal having card information on a payment card (e.g, a credit card or a bus card) approaches a card reader, a short-range mobile payment may be executed. As another example, if a mobile terminal which stores card information on an entrance card approaches an entrance card reader, an entrance approval procedure may start. A card such as a credit card, a traffic card, or an entrance card may be included in the security module in the form of applet, and the security module may store card information on the card mounted therein. Card information for a payment card may include any of a card number, a remaining amount and usage history, and the like. Card information of an entrance card may include any of a user's name, a user's number (e.g., undergraduate number or staff number), an entrance history, and the like.

When the NFC module operates in a reader mode, the mobile terminal can read data from an external tag. The data received from the external tag by the mobile terminal may be coded into the NFC Data Exchange Format defined by the NFC Forum. The NFC Forum generally defines four record types. More specifically, the NFC Forum defines four Record Type Definitions (RTDs) such as smart poster, text, Uniform Resource Identifier (URI), and general control. If the data received from the external tag is a smart poster type, the controller may execute a browser (e.g., Internet browser). If the data received from the external tag is a text type, the controller may execute a text viewer. If the data received from the external tag is a URI type, the controller may execute a browser or originate a call. If the data received from the external tag is a general control type, the controller may execute a proper operation according to control content.

In some cases in which the NFC module operates in a P2P (Peer-to-Peer) mode, the mobile terminal can execute P2P communication with another mobile terminal. In this case, Logical Link Control Protocol (LLCP) may be applied to the P2P communication. For P2P communication, connection may be generated between the mobile terminal and another mobile terminal. This connection may be categorized as a connectionless mode which ends after one packet is switched, and a connection-oriented mode in which packets are switched consecutively. For a typical P2P communication, data such as an electronic type name card, address information, a digital photo and a URL, a setup parameter for Bluetooth connection, Wi-Fi connection, etc. may be switched. The P2P mode can be effectively utilized in switching data of a small capacity, because an available distance for NFC communication is relatively short.

Figure 2:
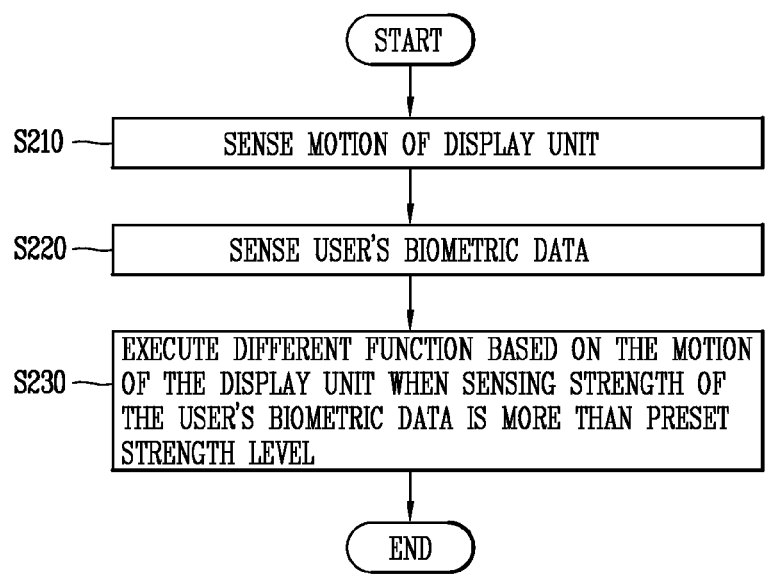
FIG. 2 is a flowchart illustrating a method for controlling a watch type terminal according to sensing strength of biometric data (i.e., strength of sensing biometric data) in a watch type terminal which is configured to sense such biometric data.
Figure 3:
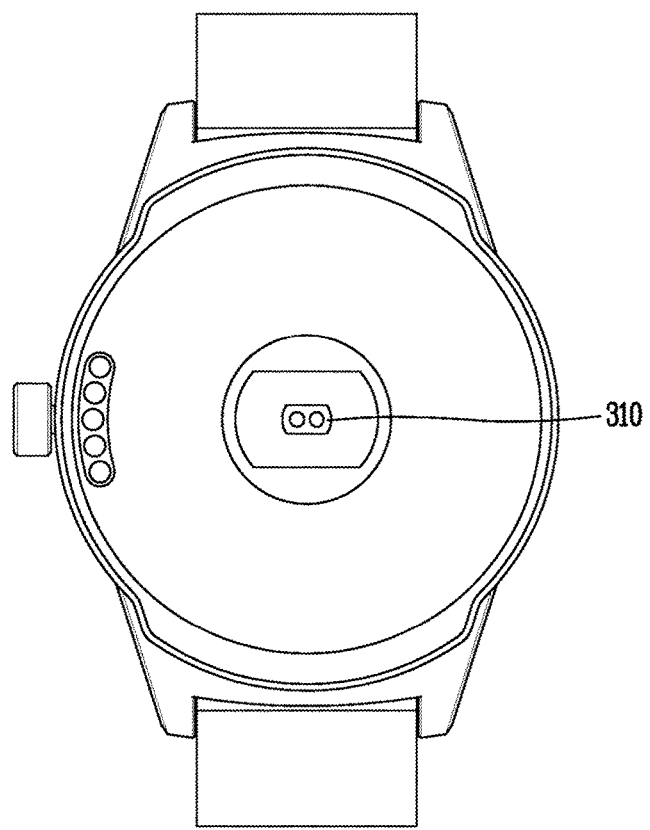
FIG. 3 is a view illustrating an arrangement of a sensing unit that is provided in a watch type terminal for sensing biometric data.
Figure 4A:
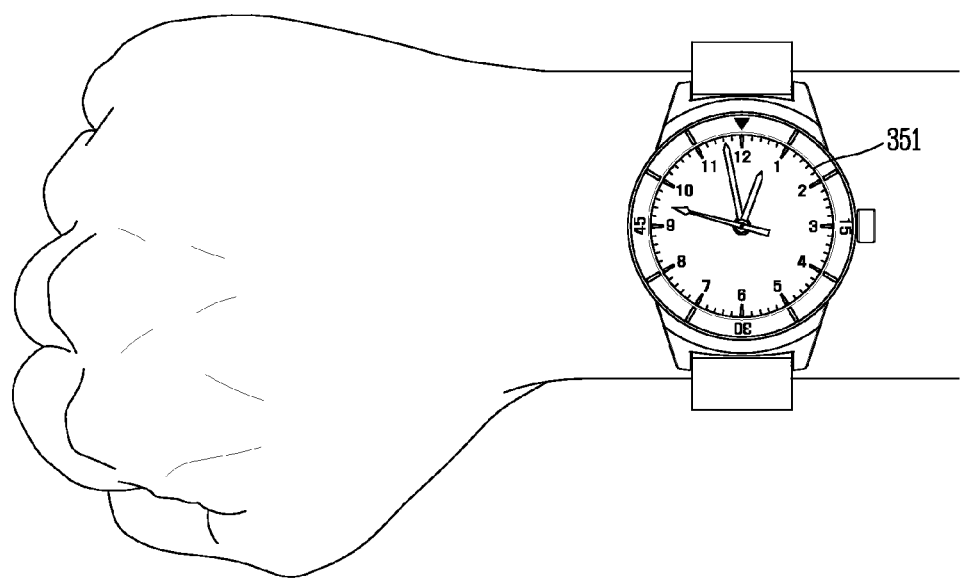
FIGS. 4A, 4B and 4C are conceptual views illustrating forms that a watch type terminal is worn on a user's wrist.
Figure 4B:
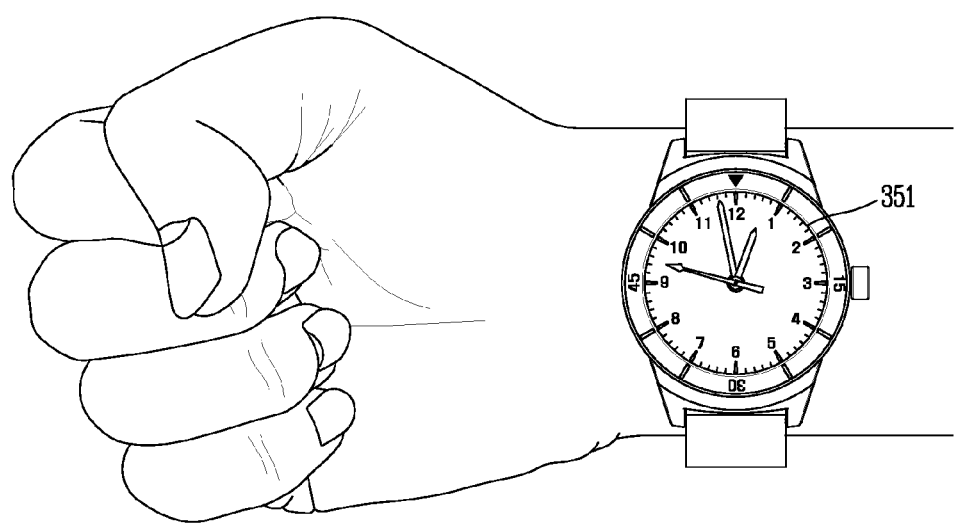
Figure 4C:
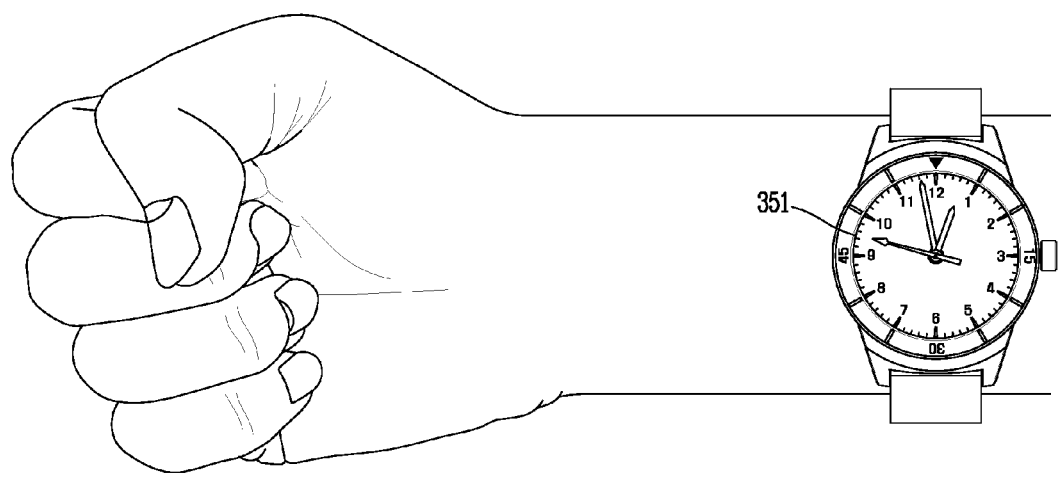
Figure 5A:
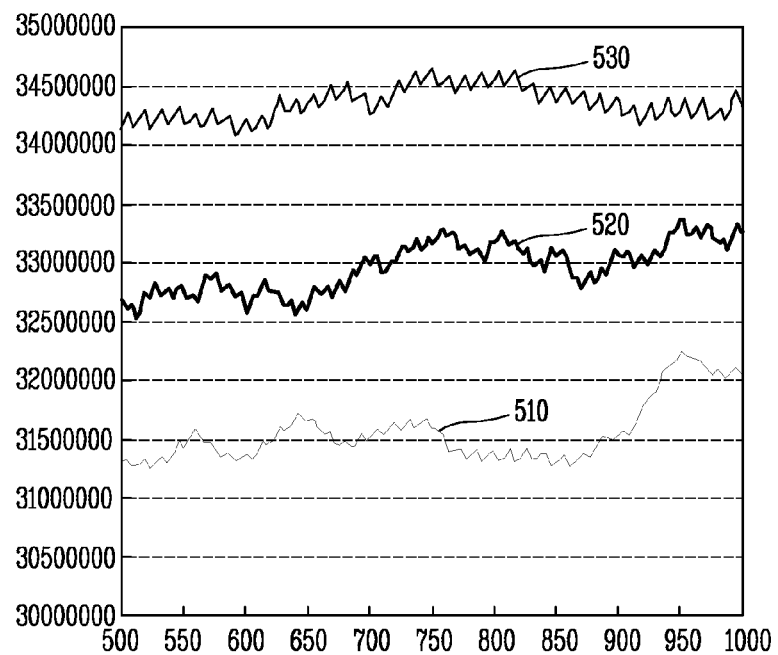
FIG. 5A is a graph illustrating sensing strength of biometric data according to a worn position of a watch type terminal on a user's wrist.
Figure 5B:
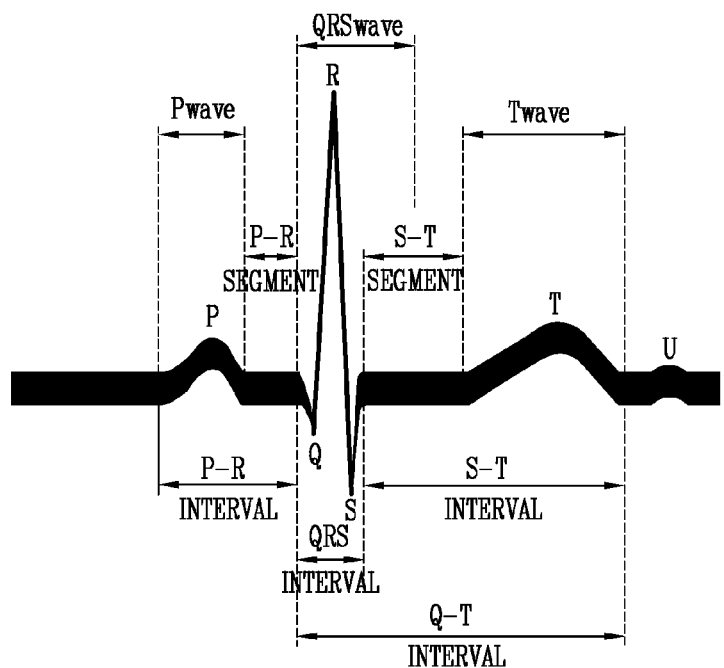
FIG. 5B is a graph illustrating waveforms of biometric data sensed in a watch type terminal.
Figure 6A:
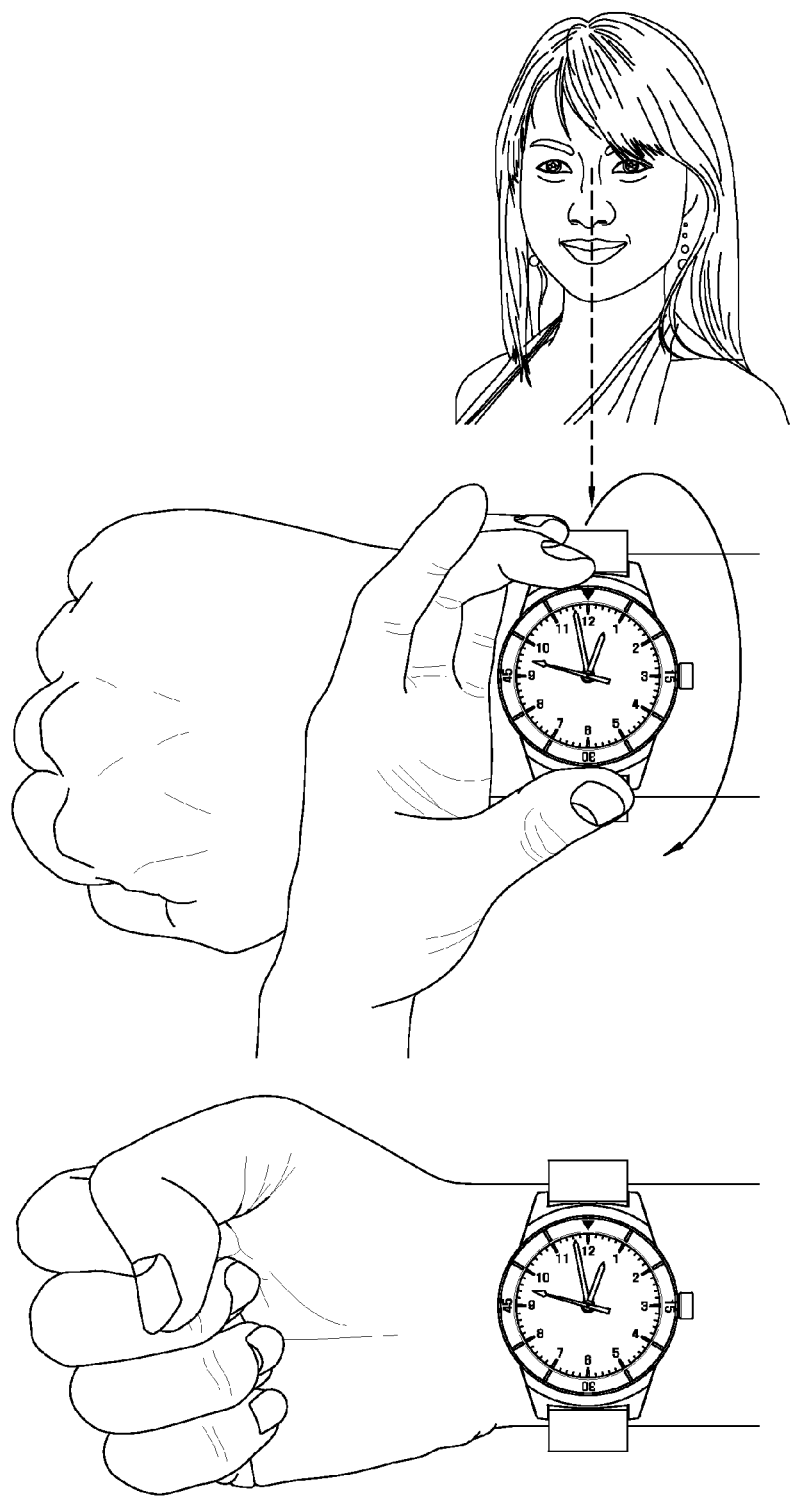
FIGS. 6A, 6B and 7 are conceptual views illustrating the control method illustrated in FIG. 2.
Figure 6B:
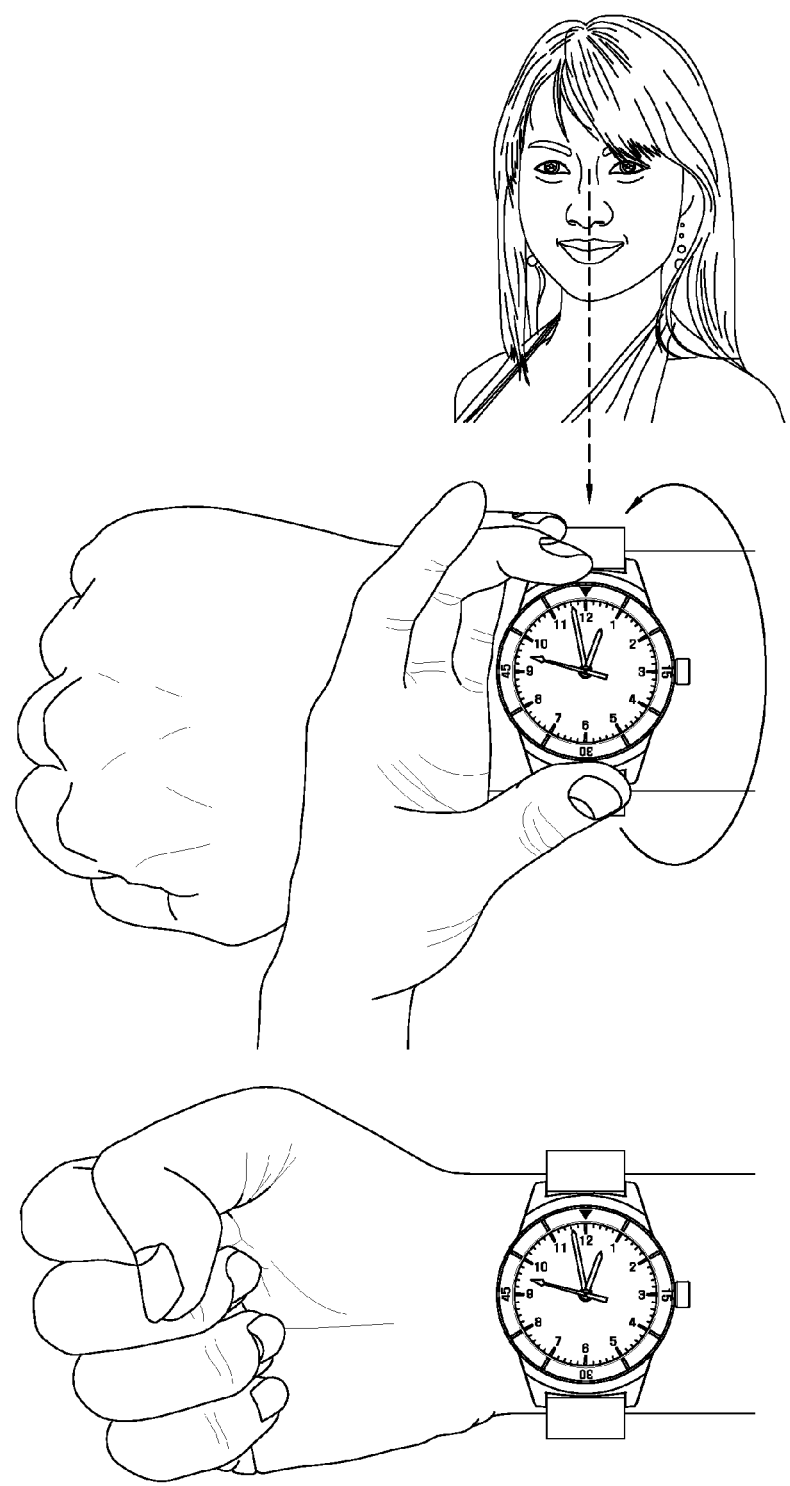
Figure 7:
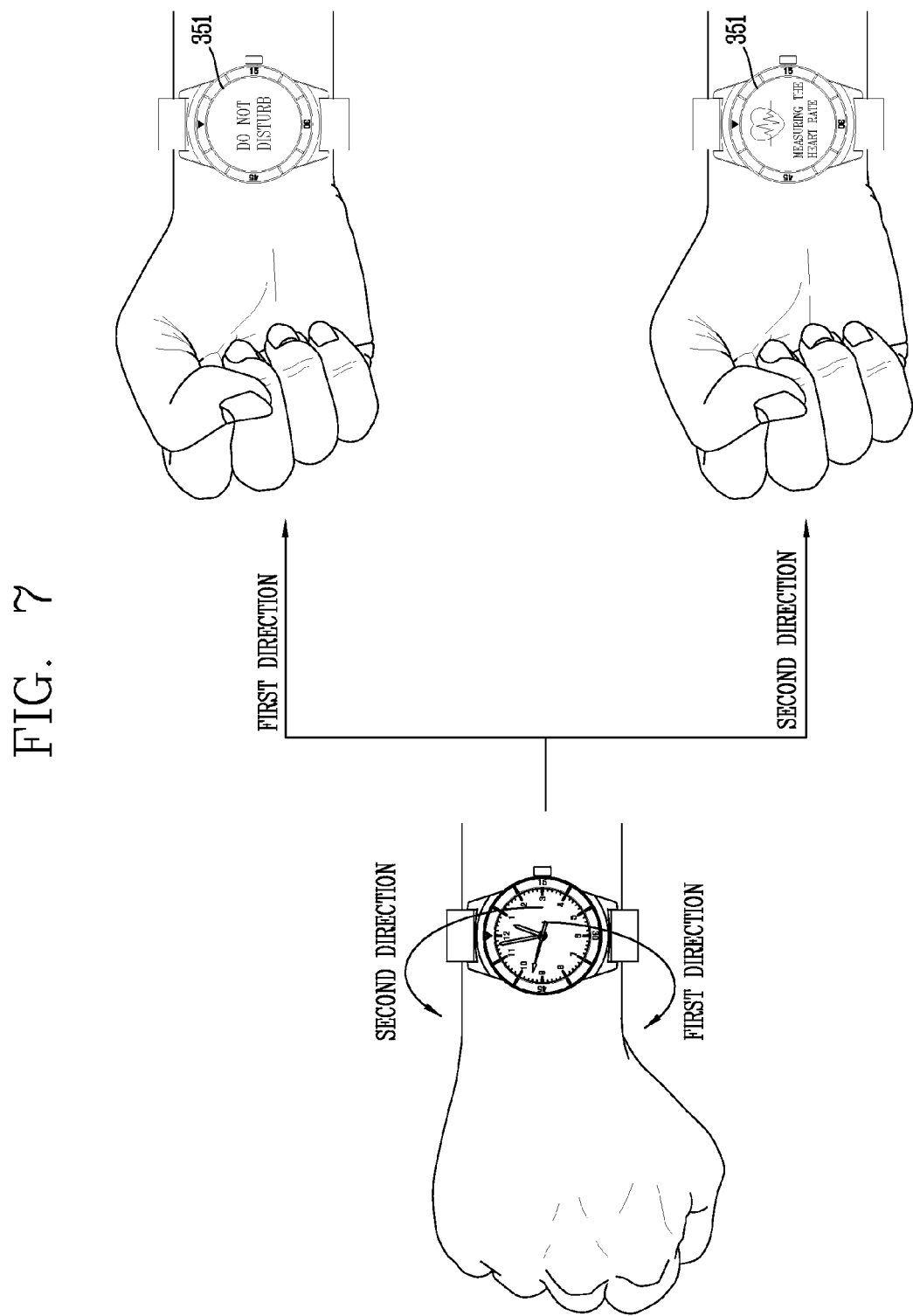

Hereinafter, description will be given of a method of providing various functions according to biometric data (biometric information) in a watch type terminal configured to sense the biometric data, with reference to the accompanying drawings. FIG. 2 is a flowchart illustrating a method for controlling a watch type terminal according to sensing strength of biometric data in a watch type terminal which is configured to sense such biometric data. FIG. 3 is a view illustrating an arrangement of a sensing unit that is provided in a watch type terminal for sensing biometric data. FIGS. 4A to 4C are conceptual views illustrating forms that a watch type terminal is worn on a user's wrist. FIG. 5A is a graph illustrating sensing strength of biometric data according to a worn position of a watch type terminal on a user's wrist. FIG. 5B is a graph illustrating waveforms of biometric data sensed in a watch type terminal. FIGS. 6A, 6B and 7 are conceptual views illustrating the control method illustrated in FIG. 2.

A watch type terminal according to the present invention may include at least one of a main body 301, a band 302 connected to the main body 301 to be wearable on a wrist, a display unit 351, a first sensing unit 310, a second sensing unit (not illustrated), and a controller 180 provided at the main body 301. Also, the watch type terminal may further include one or more of those components illustrated in FIG. 1A.

The first sensing unit 310 may be configured to sense user's biometric data (or biometric information). For example, the first sensing unit 310 may include various sensors for sensing the biometric data, such as an electrocardiogram (ECG) sensor, a photo plethysmogram (PPG) sensor, a bioelectrical impedance (BIA) sensor and the like.

The user's biometric data may include at least one information of ECG, a body mass index (BMI), body temperature, heart rate variability (HRV), oxygen saturation, a pulse transit time, a pulse rate (or a heart rate), pulse sensing strength, and a pulse waveform. Hereinafter, description will be given of an example that the user's biometric data includes at least one of the pulse sensing strength and the pulse waveform, but the same or similar method may be applicable to various types of user's biometric data in the present invention.

The first sensing unit 310 may be disposed on an area of the main body 301 to be located proximate to or come in contact with at least part of the user's body, to sense the user's biometric data in a manner of being located proximate to or coming in contact with the at least part of the user's body.

For example, the first sensing unit 310 may be located at an opposite area to an area where the display unit 351 is disposed of an entire area of the main body 301. That is, when the display unit 351 is located on a front surface of the main body 301, the first sensing unit 310 may be disposed on a rear surface of the main body 310. For example, as illustrated in FIG. 3, the first sensing unit 310 may be disposed on the rear surface of the main body 301.

The watch type terminal disclosed herein may not include the main body 301 having the display unit 351, but have a form that the display unit 351 is directly connected to the band 302. In this instance, the first sensing unit 310 may be disposed in an opposite direction (e.g., a direction of a rear surface of the display unit 351), which is opposite to a direction in which an area of the display unit 351 for outputting screen information (e.g., a direction of a front surface of the display unit 351) is located.

Meanwhile, the foregoing description has been given of the case where the first sensing unit 310 is disposed on the rear surface of the display unit 351 or the rear surface of the main body 301. However, the present invention may not be limited to this, but the first sensing unit 310 may also be disposed on various positions, such as a band, a fastener and the like of the watch type terminal, in order for the first sensing unit 310 to be proximate to or contactable with at least part of the user's body.

The second sensing unit may be configured to sense a movement or motion of the watch type terminal. For example, the second sensing unit may be a motion recognition sensor which includes at least one of an acceleration sensor, a tilt sensor and a gyro sensor.

The controller 180 may control the watch type terminal to execute a preset function, on the basis of information received from the first and second sensing units. For example, the controller 180 may activate or deactivate the display unit 351 based on information received from the first and second sensing units.

So far, each component of the watch type terminal disclosed herein has been described. Hereinafter, more detailed description will be given of a method of performing different functions according to biometric data in a watch type terminal according to the present invention, with reference to the accompanying drawings.

First, referring to FIG. 2, the watch type terminal disclosed herein may sense its motion or movement (S120).

The controller 180 may sense a motion of the watch type terminal through the second sensing unit. The motion of the watch type terminal may be a rotary motion that the watch type terminal is rotated centering on the user's wrist with the terminal worn thereon as a rotation shaft, or a linear motion that the watch type terminal is linearly moved on the user's wrist with the terminal worn thereon.

The controller 180 may activate or deactivate the second sensing unit in association with the sensing of the motion of the watch type terminal, in response to a user's request or an execution of a specific function.

For example, upon receiving a user's request for sensing a motion of the watch type terminal from a user of the watch type terminal, the controller 180 may activate the second sensing unit to measure (detect or sense) the motion of the watch type terminal. Also, when receiving a user's request for preventing the sensing of the motion of the watch type terminal from the user of the watch type terminal, the controller 180 may deactivate the second sensing unit not to measure the user's biometric data.

As another example, the controller 180 may activate or deactivate the second sensing unit in response to an execution of a specific function. The specific function may be a function using the motion of the watch type terminal. For example, the specific function may be an exercise recording function.

The activation of the second sensing unit may refer to supplying a current to the second sensing unit such that the motion of the watch type terminal can be measured or sensed by the second sensing unit. On the other hand, the deactivation of the second sensing unit may refer to quitting a current supply to the second sensing unit such that the motion of the watch type terminal cannot be measured or sensed by the second sensing unit.

In the activated state (or active state) of the second sensing unit, the controller 180 may calculate characteristic information relating to the motion of the watch type terminal on the basis of information related to the motion of the watch type terminal when the motion of the watch type terminal is sensed.

In more detail, when the motion of the watch type terminal is a rotary motion, the controller 180 may sense and calculate at least one of a direction, a turn (or rotation) speed and the number of turns of the rotary motion. Accordingly, the controller 180 may identify (or recognize) the rotary motion of the watch type terminal. For example, in case where the watch type terminal worn on the user's right wrist is rotated centering on the user's right wrist as a rotation shaft, in a state that the display unit of the watch type terminal directly faces the user's face, the controller 180 may discriminate a rotary motion in a first direction that the watch type terminal is rotated close to the user's face (see FIG. 6A) and a rotary motion in a second direction that the watch type terminal is rotated away from the user's face (see FIG. 6B) from each other.

Also, when the motion of the watch type terminal is a linear motion, the controller 180 may calculate a moving direction, a moving speed and a moving distance of the linear motion. Accordingly, the controller 180 may identify the linear motion of the watch type terminal. For example, when the watch type terminal is linearly moved, the controller 180 may discriminate a motion toward the user's elbow (see FIG. 4C) and a motion toward the user's hand from each other.

The characteristic information relating to the calculated motion may be stored simply in the memory 170, or stored in association with an application (e.g., an exercise application or a schedule management application), which relates to a preset motion of the watch type terminal.

Also, the controller 180 may determine the user's movement (or motion) based on the motion of the watch type terminal. For example, the controller 180 may determine the number of steps, a walking speed and the like of the user having the watch type terminal, on the basis of the motion of the watch type terminal.

In this instance, the controller 180 may calculate at least one of the number of steps, a walking distance and a walking speed on the basis of the user's movement sensed through the second sensing unit. For example, the controller 180 may calculate the user's walking speed and steps.

The controller 180 may activate at least one sensor for more accurately calculating the user's movement. For example, when the user's motion corresponds to a preset motion, the controller 180 may activate at least one sensor relating to the user's motion.

The preset motion may be defined based on the user's motion characteristic (for example, a moving speed, a moving form, etc.). For example, the preset motion may be a motion that the user's motion has a specific moving speed. The preset motion may be preset when the watch type terminal is presented on the market or set by the user.

The at least one sensor may be at least one of a location detection sensor (e.g., GPS sensor), an acceleration sensor, a velocity sensor and a gyro sensor.

Also, while the second sensing unit is activated, the controller 180 may deactivate the second sensing unit, in response to reception of a user's control command for deactivating the second sensing unit. In this instance, the controller 180 may cut off a current supplied to the second sensing unit.

Hereinafter, description will be given of the rotary motion or the linear motion of the watch type terminal. However, the present invention may not be limited to this, but the same or similar control method may be applicable to various motions.

The watch type terminal disclosed herein may also sense user's biometric data (or biometric information) (S220).

The controller 180 may receive the user's biometric data through the first sensing unit 310. The biometric data may further include sensing strength of the biometric data (i.e., strength of sensing the biometric data) and waveform information. Also, the controller 180 may calculate the sensing strength and waveform information regarding the user's biometric data received through the first sensing unit 310.

The controller 180 may activate or deactivate the first sensing unit 310 to sense the user's biometric data, in response to a user request. For example, when receiving a user request for sensing the biometric data from the user having the watch type terminal, the controller 180 may activate the first sensing unit 310 to measure the user's biometric data.

On the other hand, when receiving a user request for not sensing the user's biometric data from the user of the watch type terminal, the controller 180 may deactivate the first sensing unit 310 not to measure the user's biometric data.

The activation of the first sensing unit 310 may refer to supplying a current to the first sensing unit 310 to measure the motion of the watch type terminal. On the other hand, the deactivation of the first sensing unit 310 may refer to quitting a current supply to the first sensing unit 310 not to measure the motion of the watch type terminal.

When the first sensing unit 310 is activated, the controller 180 may continuously measure the user's biometric data at a preset period, or measure the user's biometric data when a preset condition is met. The preset condition may be a condition that the motion of the watch type terminal matches a preset motion.

Meanwhile, sensing strength of the user's biometric data may vary according to a contact or a proximity position at which the first sensing unit 310 comes in contact with or is located close to the user's body.

In more detail, the watch type terminal disclosed herein which is worn on the user's wrist may be located proximate to or contactable with at least part of the user's wrist. Here, the watch type terminal may be located proximate to or come in contact with one of an outer side and an inner side of the user's wrist. For example, referring to FIG. 4A, the watch type terminal may be worn in such a manner that the display unit 351 of the watch type terminal is located at the outer side of the user's wrist. As another example, referring to FIG. 4B, the watch type terminal may be worn in such a manner that the display unit 351 of the watch type terminal is located at the inner side of the user's wrist.

The watch type terminal disclosed herein may also be located close to or far away from the user's elbow. For example, the watch type terminal may be located far away from the elbow as illustrated in FIG. 4B, or close to the elbow as illustrated in FIG. 4C. Also, unlike the examples illustrated in FIGS. 4B and 4C, the watch type terminal may be located close to or away from the elbow while being located proximate to or coming in contact with the outer side of the wrist.

The sensing strength of the user's biometric data may vary depending on a position at which the watch type terminal is located proximate to or comes in contact with the user's wrist. The sensing strength of the biometric data may be signal strength of a biometric signal which indicates the sensed biometric data.

The signal strength of the biometric signal may be decided by at least one of average amplitude intensity, minimum amplitude intensity, and a signal to noise ratio (SNR). In more detail, the biometric signal may have high signal strength when the average amplitude intensity, the minimum amplitude intensity and the SNR are greater, while having lower strength when the average amplitude intensity, the minimum amplitude intensity and the SNR are smaller.

The signal strength of the biometric signal may be sensed more strongly at the inner side than at the outer side of the user's wrist. Also, the signal strength of the biometric signal may be more strongly sensed upon being closer to the user's heart.

For example, referring to FIG. 5A, the signal strength of the user's biometric data may increase in the order of i) a case where the watch type terminal is proximate to or comes in contact with the outer side of the user's wrist (510), ii) a case where the watch type terminal is located proximate to or comes in contact with the inner side of the user's wrist at a position far away from the user's elbow (520), and iii) a case where the watch type terminal is located proximate to or comes in contact with the inner side of the user's wrist at a position close to the user's elbow (530).

Accordingly, the controller 180 may determine that the sensing strength of the biometric data is high when the user's biometric signal has high signal strength, while determining that the sensing strength of the biometric data is low when the user's biometric signal has low strength.

That is, the present invention may increase the sensing strength of the user's biometric data when the user moves the watch type terminal from outer to inner sides of the wrist or moves the watch type terminal close to the elbow.

The biometric data may also be different depending on each person or user. That is, the biometric data may be used as identification information for each person or user.

In more detail, the waveform of the biometric signal indicating the user's biometric data may individually differ. More specifically, waveforms of biometric signals of different users may be different from one another in at least one of heart rate variability (HRV), time variation of the waveform and unusual heartbeat shape. For example, referring to FIG. 5B, the waveform of the biometric signal may include atrial depolarization (P wave), ventricular depolarization (ORS wave) and ventricular repolarization (T wave). Here, the controller 180 may measure the HRV of the waveform of the biometric signal, and identify a user based on the measured HRV.

Meanwhile, the steps S210 and S220 may be carried out in a sequential manner, in a reverse order or in a simultaneous manner.

The watch type terminal according to the present invention may execute a different function on the basis of a motion thereof when the sensing strength of the user's biometric data is more than a preset strength level after sensing the user's biometric data (S230).

The controller 180 may sense the user's biometric data of a preset strength level or more. For example, when the watch type terminal is worn on the inner side of the user's wrist, the controller 180 may sense the user's biometric data of a preset strength level or more. The preset strength level may be preset when the watch type terminal is released on the market or set by the user. When the preset strength level is set by the user, the user may previously input and store the biometric data through the first sensing unit 310 of the watch type terminal.

When the sensing strength of the biometric data is more than the preset strength level, the controller 180 may execute a different function on the basis of the motion of the watch type terminal.

The controller 180 may execute a different function on the basis of one of a motion before it is sensed that the sensing strength of the biometric data is more than the preset strength level and a motion after it is sensed that the sensing strength of the biometric data is more than the preset strength level. For example, when the sensing strength of the biometric data is more than the preset strength level, the controller 180 may determine a motion of the watch type terminal, which has been sensed in a time section until before a predetermined time, on the basis of a time point when the sensing strength of the biometric data is changed into the preset strength level or more. As another example, the controller 180 may determine a motion of the watch type terminal, which has been sensed until a time point after a predetermined time from the time point when the sensing strength of the biometric data is changed into the preset strength level or more.

The different function may include, for example, a function of entering a specific mode in which at least one of applications preinstalled in the watch type terminal is executable, a function of executing one of the applications preinstalled in the watch type terminal, a function of changing setting information relating to the watch type terminal, a function of activating specific components of the watch type terminal, and the like.

The function of entering the specific mode may be a function of controlling a state of a watch type terminal such that an execution of the other applications except for at least one application is restricted. Also, the function of entering the specific mode may be a function of controlling a state of a watch type terminal such that functions associated with at least one application can automatically be executed.

The function of changing the setting information relating to the watch type terminal may be a function of changing control method information relating to the display unit 351 of the watch type terminal (e.g., a control method of deciding an activation of the display unit based on a motion of a main body, a control method of deciding the activation of the display unit irrespective of the motion of the main body, etc.), information relating to a method of outputting notification information of the watch type terminal (e.g., a visual output method, an audible output method, a tactile output method, etc.), wireless communication method information (e.g., LTE, 3G/4G, WiFi, etc.), input method setting information (e.g., a keyboard type, a gesture type, an eye-tracking, etc.), and the like.

The function of activating the components of the watch type terminal may include activation/deactivation of a data communication unit, NRC activation/deactivation, MST activation/deactivation, Bluetooth activation/deactivation, GPS activation/deactivation, sensor activation/deactivation and the like.

The functions to be executed according to the motion of the watch type terminal may be set by a user or preset at the initialization of the watch type terminal. The functions to be executed according to the motion of the watch type terminal may be decided based on status information relating to the watch type terminal. The status information relating to the watch type terminal may be location information, motion information, and the like, relating to the watch type terminal.

That is, referring to FIG. 7, in case where the sensing strength of the user's biometric data is more than a preset strength level, the controller 180 may execute a first function when the motion of the watch type terminal is a first motion, and second function when the motion of the watch type terminal is a second motion.

For example, as illustrated in FIG. 7, after it is sensed that the sensing strength of the user's biometric data is more than the preset strength level, when the motion of the watch type terminal is a motion of rotating in a first direction centering on an arm between the user's wrist and elbow as a rotation shaft, the controller 180 may execute a function associated with privacy. For example, when the watch type terminal is worn on the user's right wrist, the first direction may be a clockwise direction of rotating the watch type terminal centering on the arm between the wrist and the elbow as the rotation shaft. Explaining this based on the user's front face, in a state where the watch type terminal is worn on the user's right wrist and the display unit of the watch type terminal faces the user's front face, the first direction may be a direction of moving close to the user's front face.

The privacy-related function may be a function of using personal information (e.g., a function of entering a payment mode, a message function, etc.) or a function requiring for private setting of a person (e.g., a function of entering a study mode, etc.). The function of entering the payment mode may be a function of performing payment using the watch type terminal, and the function of entering the study mode may be a function of restricting an output of notification information within a specific time section or measuring a user's stress index. Here, the mode may refer to a state of a watch type terminal for providing at least one preset function. For example, the study mode may be a state of a watch type terminal of providing a function of restricting an output of notification information, a function of measuring a stress index, a function of blocking a network, and the like.

As another example, referring to FIG. 7, after it is sensed that the sensing strength of the user's biometric data is more than the preset strength level, when the motion of the watch type terminal is a motion of rotating in a second direction centering on the user's wrist as a rotation shaft, the controller 180 may execute a function associated with the user's motion. For example, when the watch type terminal is worn on the user's right wrist, the second direction may be a counterclockwise direction of rotating the watch type terminal centering on the arm between the user's wrist and elbow as the rotation shaft. Explaining this based on the user's front face, in a state where the watch type terminal is worn on the user's right wrist and the display unit of the watch type terminal faces the user's front face, the second direction may be a direction that the display unit is getting away from the user's front face.

The function associated with the user's motion may be a function of entering a driving mode or a function of entering an exercise mode. The driving mode may include functions associated with running or driving of a vehicle, for example, a function of activating a display unit, and a function of measuring driving safety. The exercise mode may include functions of measuring and recording the user's biometric data, such as changes in a pulse rate and the like, and information regarding the user's motion in the watch type terminal.

The function executed according to the motion of the watch type terminal may be preset at the initialization of the watch type terminal or set by the user. Also, the user may freely change the function executed according to the motion of the watch type terminal.

Meanwhile, the foregoing description has been given of the different functions which are executed according to the sensing strength of the user's biometric data and the motion of the watch type terminal. Also, the present invention may execute different functions by further considering a preset condition, as well as the sensing strength of the user's biometric data and the motion of the watch type terminal.

In more detail, the controller 180 may decide a function executed according to the motion of the watch type terminal, on the basis of a preset condition. The preset condition may be a condition associated with the user's motion or a condition associated with status information regarding the watch type terminal. For example, the preset condition may be a condition that the watch type terminal is present within a vehicle or the user's motion is a running motion.

That is, under a state that the preset condition is met, when the sensing strength of the user's biometric data is more than a preset strength level and the motion of the watch type terminal corresponds to a preset motion, the controller 180 may execute a function associated with the preset condition. For example, under the state that the watch type terminal is present within the vehicle, when the sensing strength of the user's biometric data is more than a preset strength level and the motion of the watch type terminal is a rotary motion having a second direction, the controller 180 may execute a driving mode.

On the other hand, under the state that the user's motion is a running motion, when the sensing strength of the user's biometric data is more than a preset strength level and the motion of the watch type terminal is a rotary motion having a second direction, the controller 180 may execute an exercise mode.

Also, when a specific function has been executed as the sensing strength of the user's biometric data is more than a preset strength level and the motion of the watch type terminal is a preset motion, the controller 180 may control the specific function according to the sensing strength of the user's biometric data.

For example, the controller 180 may execute a payment function as the sensing strength of the user's biometric data is more than a preset strength level and the motion of the watch type terminal is a preset motion.

When the payment function is executed, the controller 180 may decide a payment limit of the payment function according to the sensing strength of the user's biometric data. For example, the controller 180 may increase the payment limit more for higher sensing strength of the user's biometric data.

Also, while a specific function is executed as the sensing strength of the user's biometric data is more than a preset strength level and the motion of the watch type terminal is a preset motion, the controller 180 may control the specific function by using the user's biometric data as user identification information.

For example, as the sensing strength of the user's biometric data is more than a preset strength level and the motion of the watch type terminal corresponds to a preset motion, the controller 180 may execute a driving mode.

When the driving mode is executed, the controller 180 may determine the user's identification information based on the user's biometric data, and reproduce a media file associated with the identified user.

That is, the present invention can provide various functions suitable for each person by using the biometric data.

Meanwhile, under a state where a specific function has been executed as the sensing strength of the biometric data is more than a preset strength level and the motion of the watch type terminal is a preset motion, when it is sensed that the sensing strength of the biometric data is decreased below the preset strength level, the controller 180 may output notification information. The notification information may include guide information which guides the user to wear the watch type terminal at the inner side of the wrist or wear the watch type terminal by moving toward the elbow. In this instance, when the sensing strength of the biometric data is lower than the preset strength level for a preset time, the controller 180 may terminate (end) the executed specific function.

When it is sensed that the sensing strength of the biometric data is lower than the preset strength level, the controller 180 may temporarily stop the executed specific function, and output the notification information. In this instance, when the sensing strength of the biometric data is lower than the preset strength level for a preset time, the controller 180 may terminate the executed specific function. Also, when the sensing strength of the biometric data increases more than the preset strength level again within a preset time, the controller 180 may re-execute the temporarily-stopped specific function.

When it is sensed that the sensing strength of the biometric data is lower than the preset strength level, the controller 180 may immediately terminate the executed specific function without an output of notification information.

The foregoing description has been given of the method of executing a different function based on the motion of the watch type terminal when the sensing strength of the user's biometric data is more than a preset strength level. This may allow the watch type terminal to provide functions suitable for the user's intent even by considering the sensing strength of the biometric data as well as the motion of the watch type terminal.

Hereinafter, a method of providing a driving mode in a watch type terminal will be described. FIGS. 8A to 8C, 9A to 9C, 10A to 10B, 11 and 12A to 12B are conceptual views illustrating a method of providing a driving mode function in a watch type terminal.

The watch type terminal according to the present invention may execute a driving mode when sensing strength of the user's biometric data is more than a preset strength level and a motion of the watch type terminal corresponding to a preset motion. For example, when strength of sensing a user's pulse is more than a preset strength level and the watch type terminal is rotated in a second direction (e.g., a counterclockwise direction when the watch type terminal is worn on a right wrist), the controller 180 may execute a driving mode.

That is, the present invention may increase the sensing strength of the user's biometric data when the watch type terminal is moved from outer to inner sides of a wrist or moved toward a position close to an elbow.

The driving mode may be a state of a watch type terminal which executes at least one of a function of restricting an activation of a display unit according to the motion of the watch type terminal, a function of changing an output method of notification information or restricting an output of the notification information, and a function of predicting drowsiness based on driver's biometric data and measurement of carbon dioxide density (concentration or level) within a vehicle and thus outputting warning information.

Meanwhile, when a pre-recognized vehicle is sensed, the watch type terminal disclosed herein may output guide information for an execution of the driving mode. In more detail, when the pre-recognized vehicle is sensed near the watch type terminal, the controller 180 of the watch type terminal may output guide information indicating a moving method of the watch type terminal such that the driver can execute the driving mode by moving the watch type terminal. Here, the watch type terminal may recognize the vehicle through short-range communication (e.g., Bluetooth communication, NFC communication, etc.). Also, the vehicle may be a vehicle whose identification information is previously stored in the watch type terminal. That is, the vehicle may be a vehicle for which authentication has been performed with the watch type terminal. Accordingly, the present invention can help the user recognize the guide information and execute the driving mode according to the guide information. In this instance, the controller 180 may execute the driving mode when a driving mode execution request is received based on the guide information.

When the driving mode is executed, the controller 180 may execute at least one of a plurality of functions provided in the driving mode. Here, a function to be executed among those plurality of functions provided in the driving mode may be set by the user or preset when the watch type terminal is presented on the market.

Hereinafter, a method of controlling each function in the driving mode according to a motion of the watch type terminal will be described in more detail.

First, a function of restricting an activation of the display unit 351 according to the motion of the watch type terminal may refer to not changing an active and/or inactive state of the display unit 351 according to the motion of the watch type terminal. That is, the controller 180 may not change the active and/or inactive state of the display unit 351 into the inactive and/or active state even though the motion of the watch type terminal is sensed.

Here, the activation of the display unit 351 may refer to lighting on the display unit 351 and controlling the display unit 351 to output visual screen information thereon. On the other hand, the deactivation of the display unit 351 may refer to lighting off the display unit 351 and controlling the display unit 351 not to output visual screen information thereon.

In more detail, the controller 180 of the watch type terminal which is not in the driving mode may activate and/or deactivate the display unit 351 on the basis of the motion of the watch type terminal.

Figure 8A:
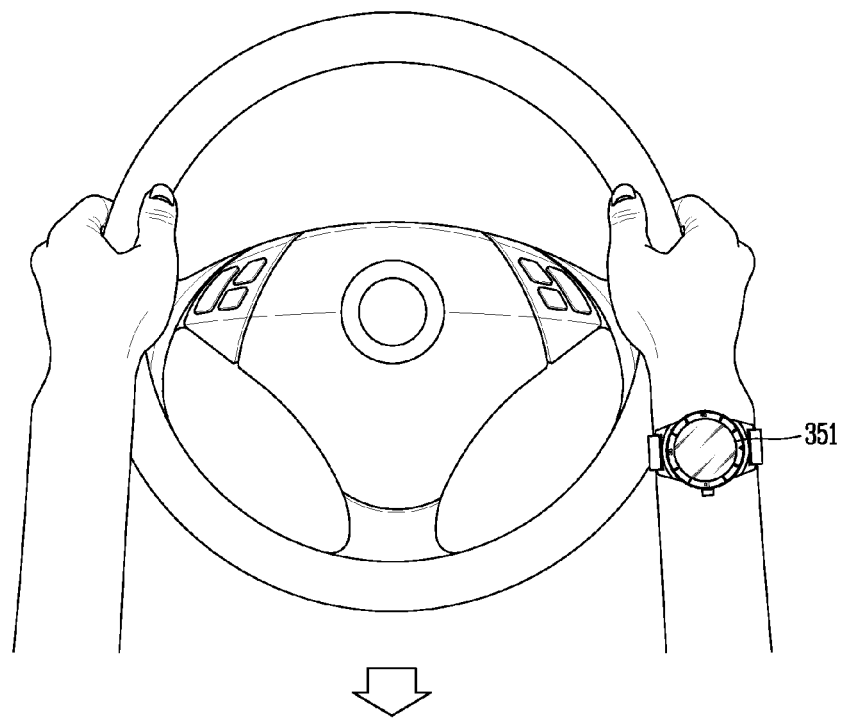
FIGS. 8A, 8B, 8C, 9A, 9B, 9C, 10A, 10B, 11, 12A and 12B are conceptual views illustrating a method of providing a driving mode function in a watch type terminal.
Figure 8A:
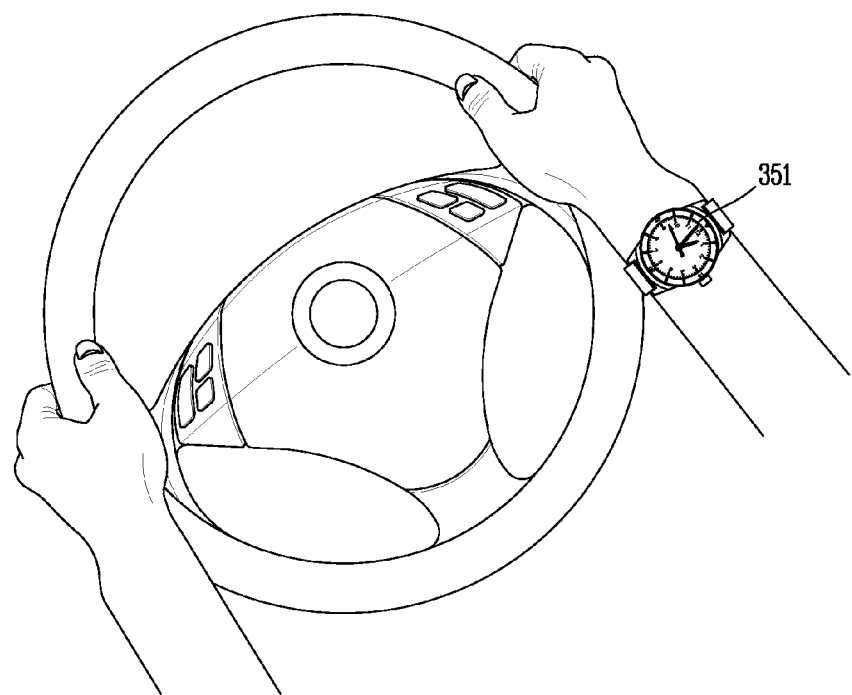
Figure 8B:
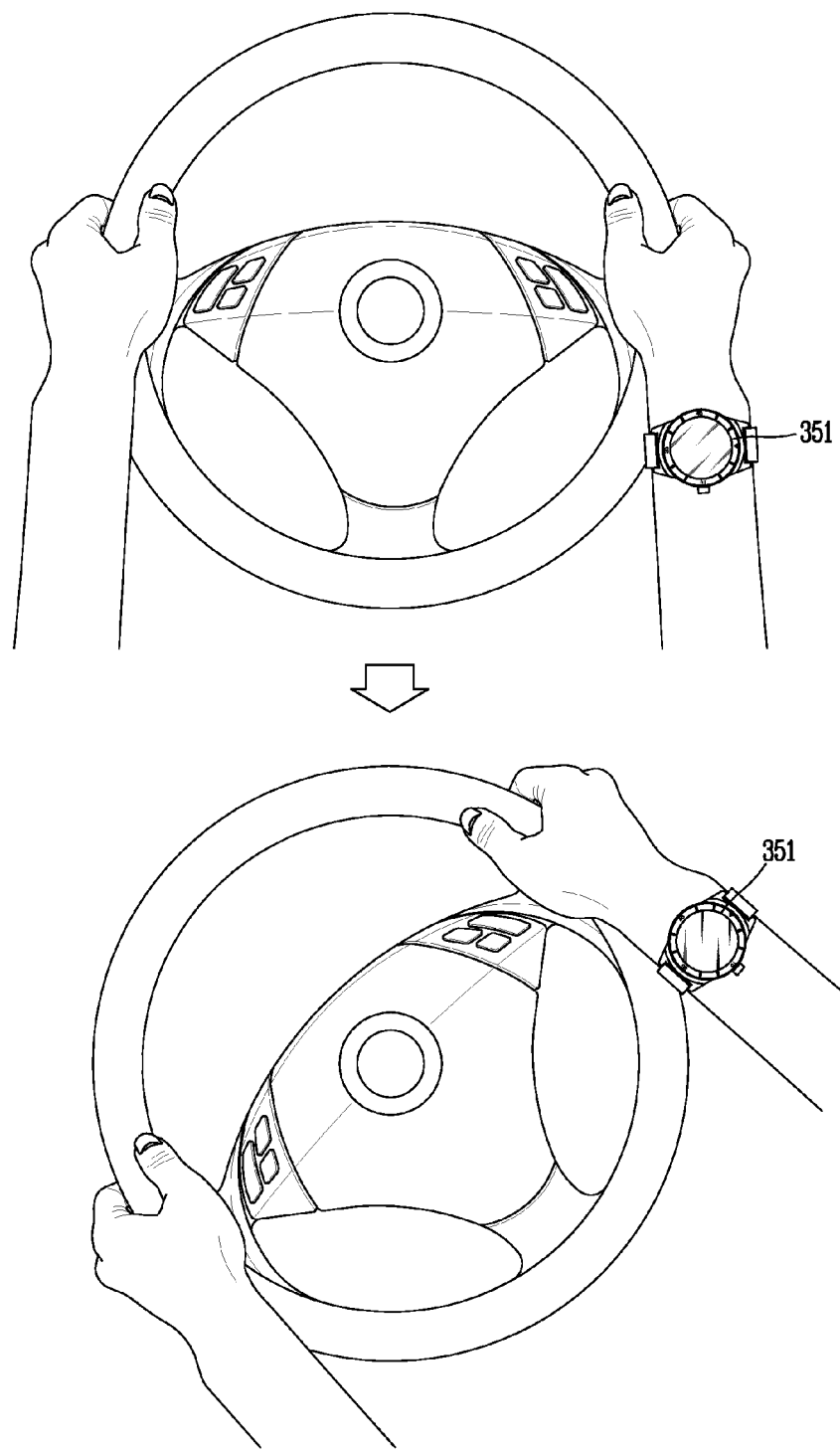

In more detail, when the motion of the watch type terminal corresponds to a first motion, the controller 180 of the watch type terminal which is not in the driving mode may control the display unit 351 to be activated. For example, as illustrated in FIG. 8A, the controller 180 may determine the motion of the watch type terminal as the first motion when the motion of the watch type terminal results from that the user's hand (or wrist) with the watch type terminal worn thereon is moved to drive a vehicle. In this instance, when the display unit 351 is in an inactive state, the controller 180 may control the display unit 351 to be turned on. Accordingly, while the user is driving after dark, the display unit 351 is unnecessarily turned on, which may cause the user to be dazzled, thereby interfering with the user's driving.

On the other hand, when the motion of the watch type terminal corresponds to a second motion, the controller 180 of the watch type terminal may control the display unit 351 to be deactivated. For example, the controller 180 may determine the motion of the watch type terminal as the second motion when the motion of the watch type terminal results from that the user's hand (or wrist) with the watch type terminal worn thereon is moved to drive a vehicle. In this instance, when the display unit 351 is in an active state, the controller 180 may control the display unit 351 to be turned off.

That is, in the watch type terminal which is not in the driving mode, the display unit 351 may automatically be turned on or off according to the motion of the watch type terminal, which causes the display unit 351 to be turned on even when the user does not want to turn it on.

Meanwhile, the controller 180 of the watch type terminal which is currently in the driving mode may restrict the activation and/or deactivation of the display unit 351 on the basis of the motion of the watch type terminal. In more detail, even when the motion of the watch type terminal, which results from that the user moves his hand (or wrist) with the watch type terminal worn thereon to drive a vehicle, corresponds to the first motion, the controller 180 of the watch type terminal in the driving mode may maintain the activated and/or deactivated state of the display unit 351. That is, the controller 180 of the watch type terminal in the driving mode may not switch the display unit 351 from a deactivated state into an activated state even though the motion of the watch type terminal is sensed.

Also, even when the motion of the watch type terminal which is made as the user's hand (or wrist) with the watch type terminal worn thereon is moved corresponds to the second motion, the controller 180 of the watch type terminal in the driving mode may maintain an activated and/or deactivated state of the display unit 351. That is, the controller 180 of the watch type terminal in the driving mode may not switch the display unit 351 from the activated state into the deactivated state even though the motion of the watch type terminal is sensed.

Figure 8C:
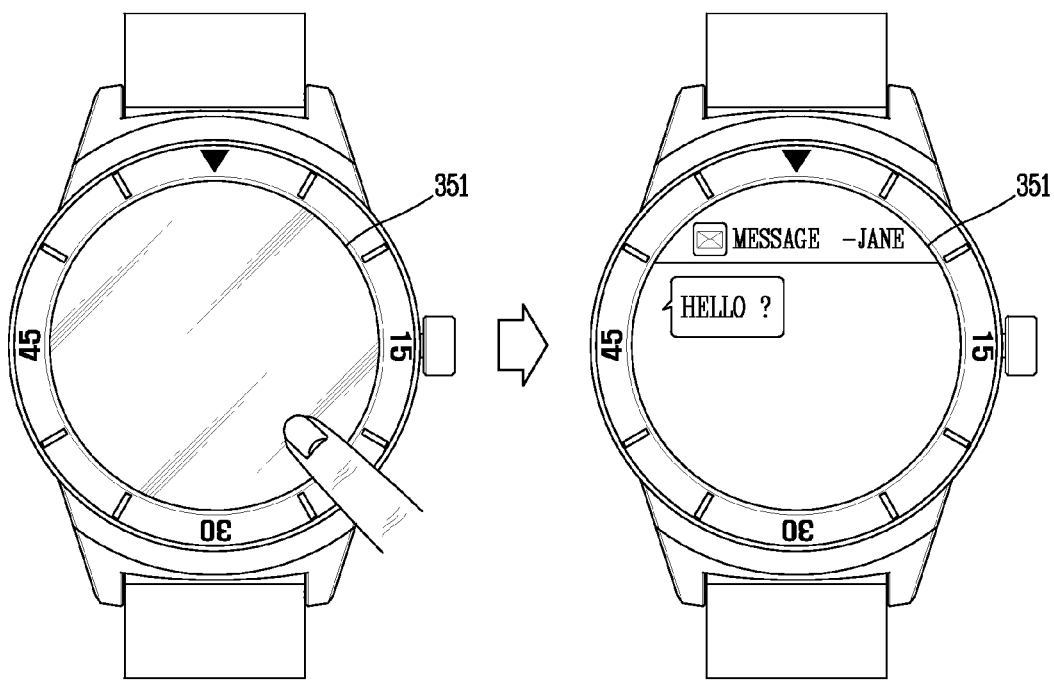

Meanwhile, in response to the user's request for activating the display unit 351, the controller 180 of the watch type terminal in the driving mode may activate the display unit 351. That is, even if the activated and/or deactivated state of the display unit 351 is not switched according to the motion of the watch type terminal, when a user request is separately received, the activation and/or deactivation of the display unit 351 may be switched. For example, as illustrated in FIG. 8C, in the deactivated state of the display unit 351, when a user's request for activating the display unit 351 is received, the controller 180 may control the display unit 351 to be activated.

That is, the present invention may allow the user to change a control method of the display unit 351 simply by an operation of rotating the watch type terminal. Accordingly, unnecessary activation and/or deactivation of the display unit according to the motion of the watch type terminal during driving at night can be prevented. Also, the driver's dazzling during the driving at night can be prevented by restricting the activation of the display unit according to the motion of the watch type terminal. Meanwhile, the foregoing description has been given of the change in the control method of the display unit 351 according to the rotary motion of the watch type terminal, but it may be easily understood by those skilled in the art that the same control method using the user's biometric data can be applied to other motions of the watch type terminal.

In the meantime, when the sensing strength of the user's biometric data is lower than a preset strength level, the controller 180 of the watch type terminal which is currently in the driving mode may output notification information related to the sensing strength of the user's biometric data. The notification information may include information indicating weak (or low) sensing strength of the user's biometric data, and guide information to guide the change in a position of the watch type terminal so as to increase the sensing strength of the user's biometric data.

Also, after the output of the notification information, when it is sensed within a preset time that the sensing strength of the biometric data is more than the preset strength level, the controller 180 may continuously execute the driving mode. On the other hand, after the output of the notification information, when the sensing strength of the biometric data sensed does not increase more than the preset strength level within the preset time, the controller 180 may terminate the executed driving mode. The termination of the driving mode may refer to executing the driving mode no more.

When the sensing strength of the user's biometric data is lower than the preset strength level, the controller 180 may output notification information related to the sensing strength of the biometric data and temporarily stop the executed driving mode. The temporary stop of the executed driving mode may refer to restricting an execution of functions associated with the driving mode.

In the temporarily-stopped state of the driving mode, after the output of the notification information, when it is sensed within a preset time that the sensing strength of the biometric data is more than the preset strength level, the controller 180 may release the temporary stop of the driving mode and then reactivate the driving mode. On the other hand, after the output of the notification information, when the sensing strength of the biometric data does not change into the preset strength level or more within the preset time, the controller 180 may terminate the executed driving mode.

Also, the controller 180 may immediately terminate the driving mode, without outputting the notification information, when it is sensed that the sensing strength of the user's biometric data is lower than the preset strength level.

When the driving mode is terminated, the controller 180 may re-execute the function of switching the display unit 351 from the active and/or inactive state into the inactive and/or active state according to the motion of the watch type terminal.

Meanwhile, the method of controlling the display unit 351 may be applied to various situations as well as the driving mode. For example, according to the present invention, the display unit 351 may be controlled such that the activation and/or deactivation of the display unit 351 according to the motion of the watch type terminal cannot be carried out when the user is at a theater. That is, in the present invention, when the sensing strength of the user's biometric data is more than a preset strength level and the motion of the watch type terminal corresponds to a preset motion, a function of restricting the activation and/or deactivation of the display unit according to the motion of the watch type terminal can be executed, instead of the driving mode. Accordingly, when ambient luminance of the watch type terminal is low, the user may control the display unit not to be turned on according to the motion of the watch type terminal, and thus the user's dazzling can be prevented. The user may also activate the display unit with low brightness in a place with low ambient luminance. This may prevent information output on the display unit from being open to others.

Figure 9A:
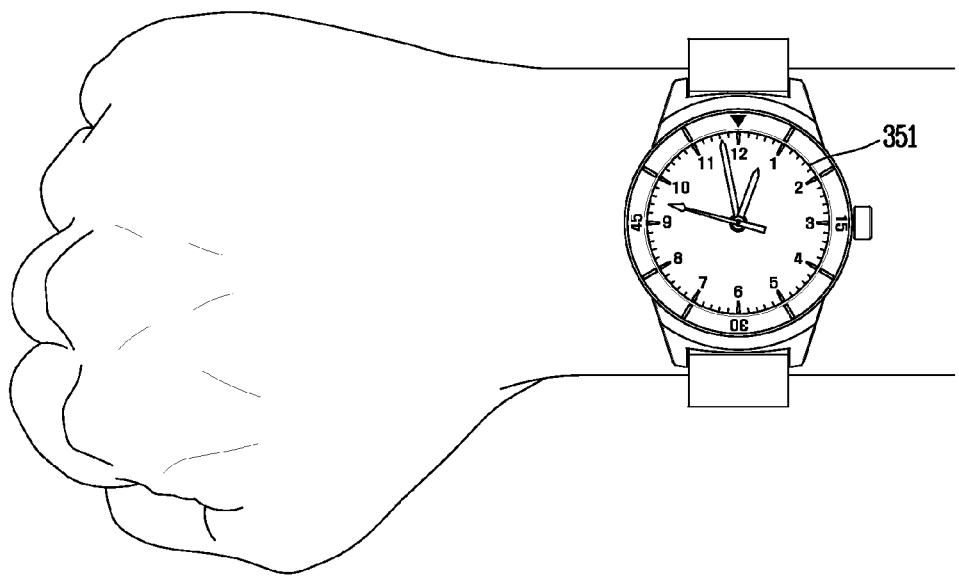
Figure 9A:
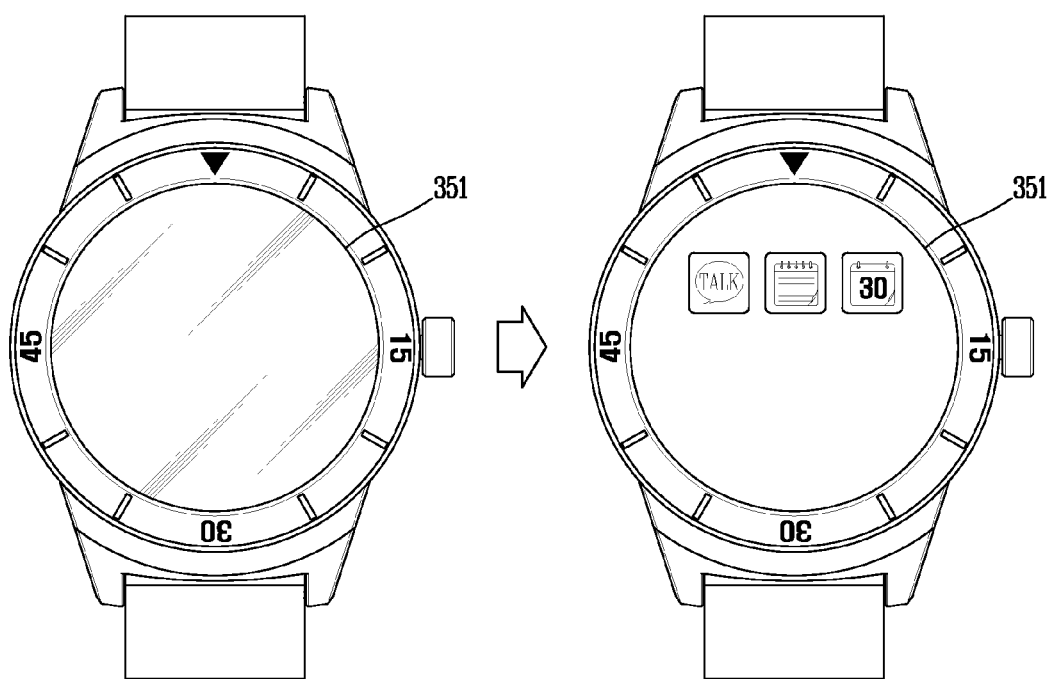

The controller 180 of the watch type terminal which is currently in the driving mode may also decide brightness of the display unit 351 according to the sensing strength of the user's biometric data. For example, as illustrated in FIG. 9A, when the driving mode is activated, the controller 180 may set the brightness of the display unit 351 to a first brightness level when the sensing strength of the user's biometric data is a first strength level. In this instance, the user may clearly view full screen information output on the display unit 351.

Figure 9B:
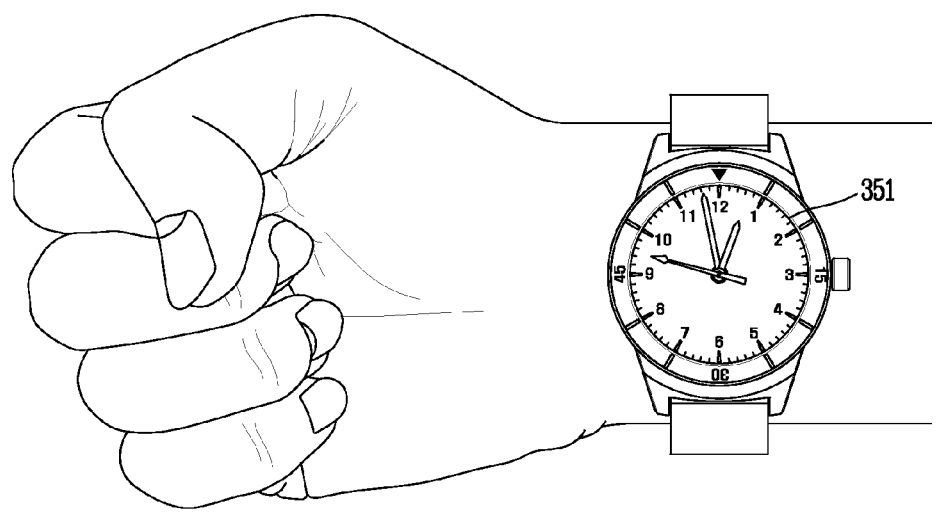
Figure 9B:
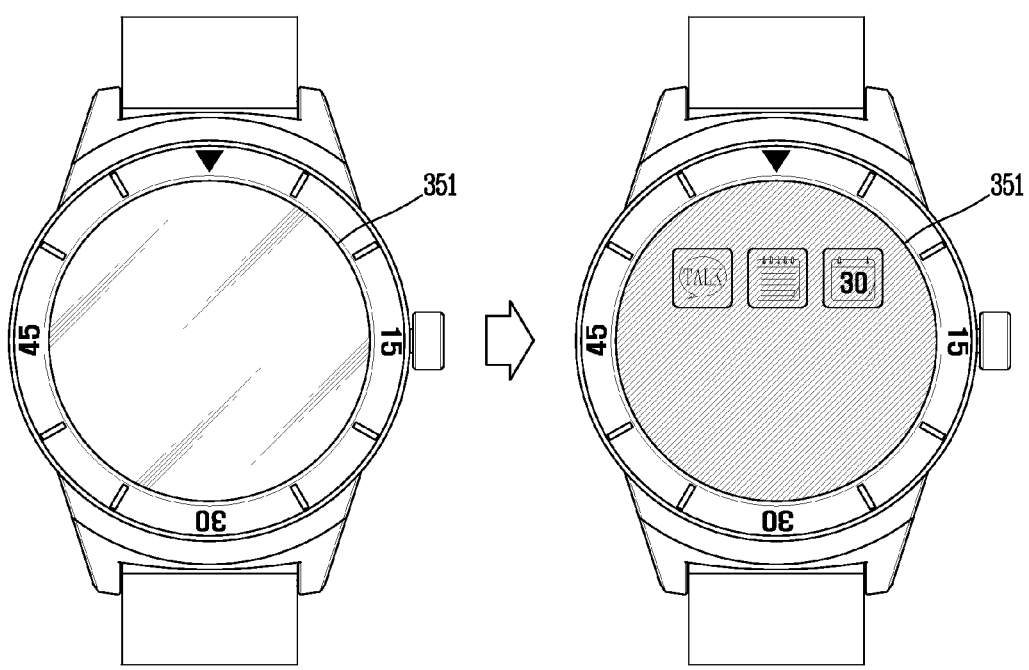

Here, as illustrated in FIG. 9B, when the sensing strength of the user's biometric data is a second strength level which is higher than the first strength level, the controller 180 may set the brightness of the display unit 351 into a second brightness level which is darker (or lower) than the first brightness level. When the brightness of the display unit 351 is lowered, the user can view screen information output on the display unit 351 with low brightness.

Figure 9C:
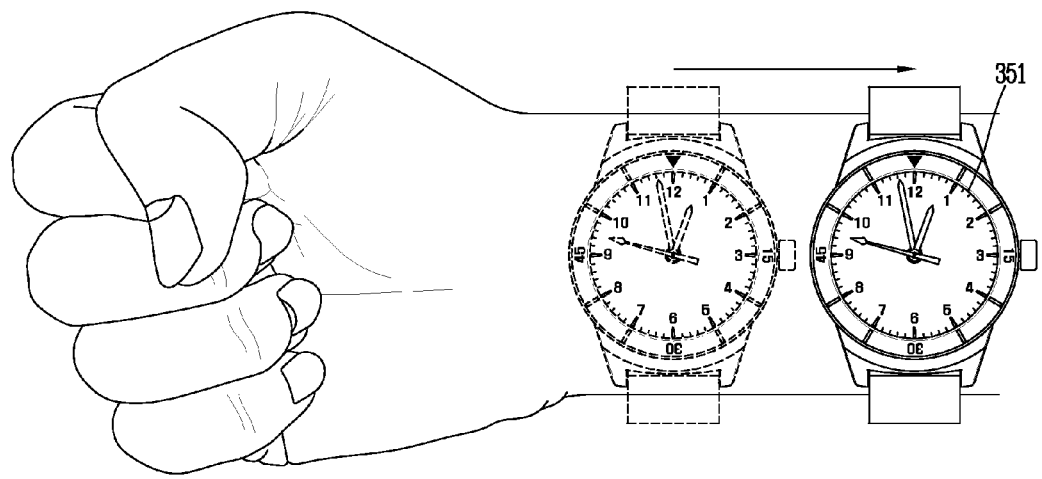
Figure 9C:
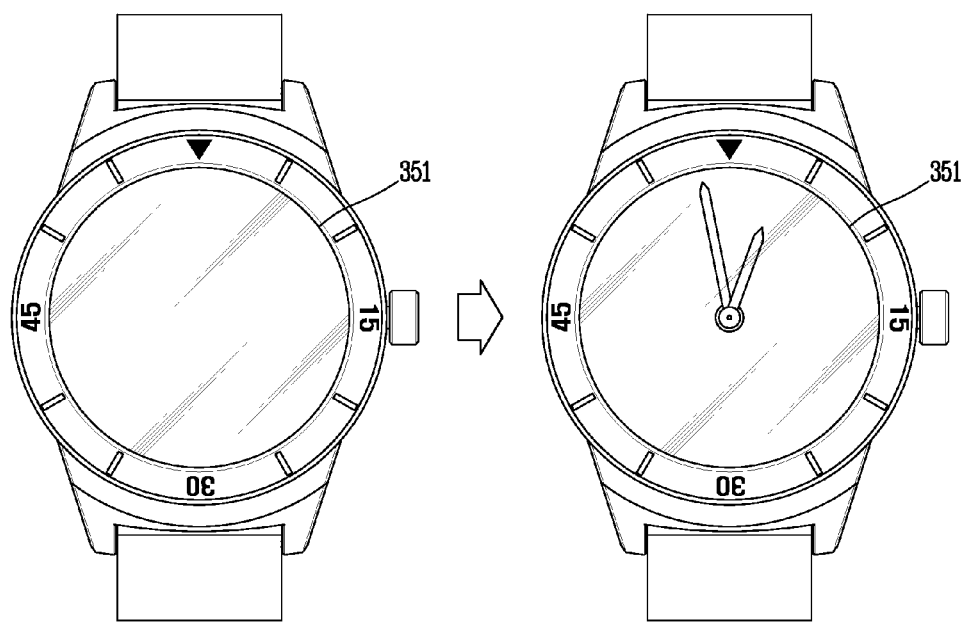

In addition, as illustrated in FIG. 9C, when the sensing strength of the user's biometric data is a third strength level which is higher than the second strength level, the controller 180 may turn off the display unit 351. In this instance, the controller 180 may not provide screen information through the display unit 351. Or, as illustrated in FIG. 9C, the controller 180 may activate at least a portion of the display unit 351 to merely output time information, and deactivate the other portion of the display unit 351 to restrict an output of information. The time information may be luminously output to ease the user's recognition even in a place where the ambient luminance of the watch type terminal is low.

Also, once the driving mode is executed, the controller 180 may decide a notification information output method, or execute a function of restricting the output of the notification information. The notification information output method may be at least one of visual, audible and tactile methods (or manners).

In more detail, when the sensing strength of the user's biometric data is more than a preset strength level and the motion of the watch type terminal is a rotary motion having a first direction (e.g., a clockwise direction when the watch type terminal is worn on a right wrist), the controller 180 may control a speaker of the watch type terminal to output notification information in an audible manner.

Figure 10A:
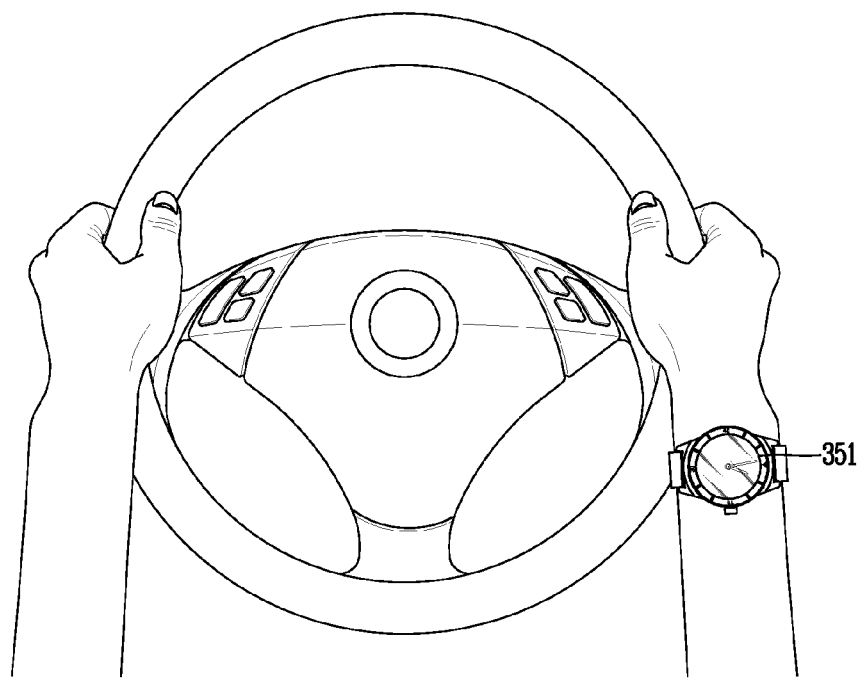
Figure 10A:
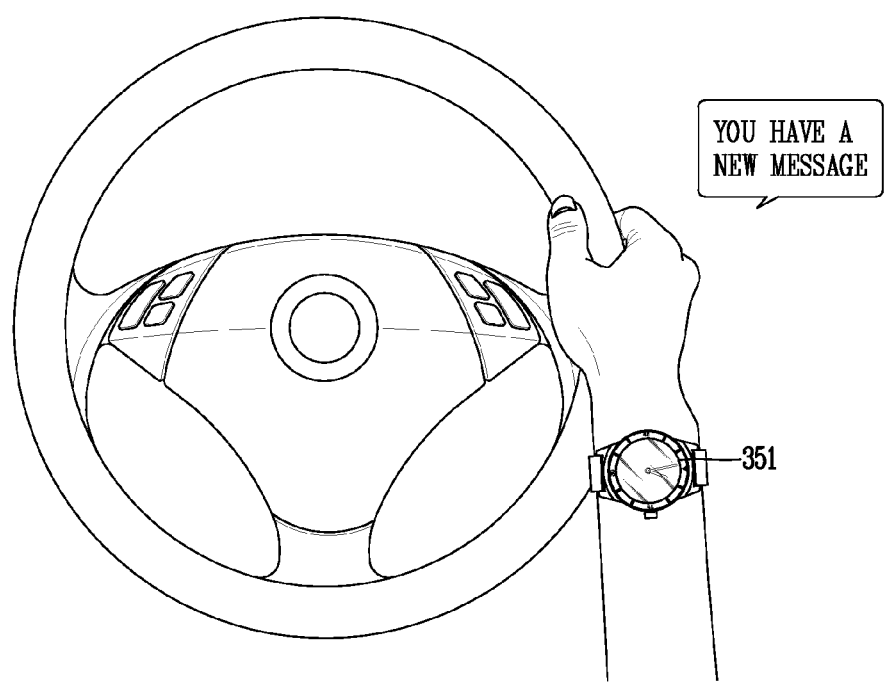

For example, as illustrated in FIG. 10A, in case where the sensing strength of the user's biometric data is more than a preset strength level and the motion of the watch type terminal is a rotary motion having a first direction, when a message is received through network communication, the controller 180 may output notification information notifying the reception of the message by voice.

Also, when the sensing strength of the user's biometric data is more than a preset strength level and the motion of the watch type terminal is a rotary motion having a second direction (e.g., a counterclockwise direction when the watch type terminal is worn on a right wrist), the controller 180 may control the watch type terminal to output notification information in a tactile manner.

Figure 10B:
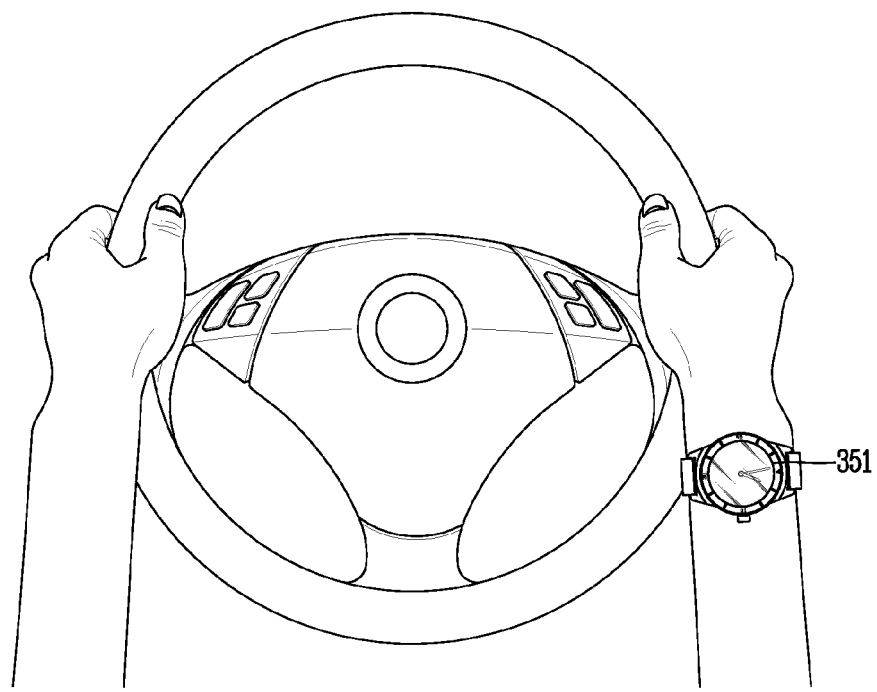
Figure 10B:
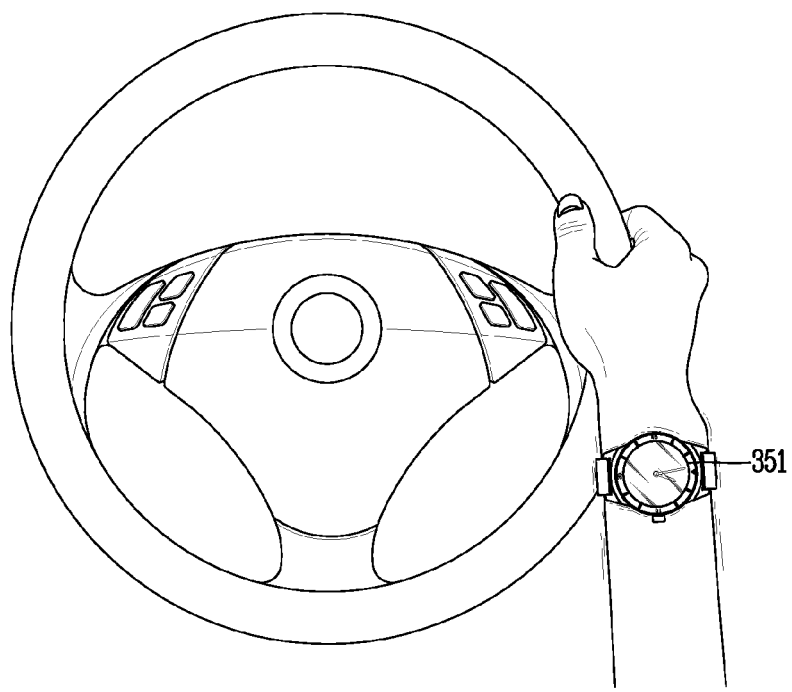

For example, as illustrated in FIG. 10B, when the sensing strength of the user's biometric data is more than the preset strength level and the motion of the watch type terminal is the rotary motion having the second direction, the controller 180 may output notification information notifying the reception of the message in a tactile manner.

Also, the present invention may be configured such that a notification information output method which has been set before execution of a driving mode can change simply by rotating the watch type terminal from outer to inner sides of a wrist. For example, under a state that the notification information output method has been set to a visual manner, when the sensing strength of the user's biometric data is more than a preset strength level and the motion of the watch type terminal corresponds to a preset motion, the controller 180 may change the notification information output method into an audible manner.

This may allow for changing the notification information output method set before the execution of the driving mode simply by rotating the watch type terminal from the outer to inner sides of the wrist.

The present invention may also allow for deciding the notification information output method in different manners according to a rotary motion of the watch type terminal, so as to provide the user with more various options. That is, the user may set notification information to be output in an audible manner so as to recognize a reception of a message even without viewing the watch type terminal when there is no fellow passenger in a vehicle, whiling setting the notification information to be output in a tactile manner such that a fellow passenger cannot recognize a reception of a message when there is the fellow passenger in the vehicle.

Also, when the driving mode is executed, the controller 180 may restrict an output of notification information. In more detail, when the driving mode is executed, the controller 180 may restrict an output of notification information, which notifies an event generation, on the basis of information related to driving of a vehicle.

The information related to the driving of the vehicle may be driving speed information of the vehicle. Also, the information related to the driving of the vehicle may be calculated based on a location information module of the watch type terminal and time information, or received from the vehicle through short-range communication.

The event is an event generated from at least one of a plurality of applications installed in the watch type terminal, and examples of the event may include an event of receiving a call signal or message from an external terminal, a schedule management event and the like.

Figure 11:
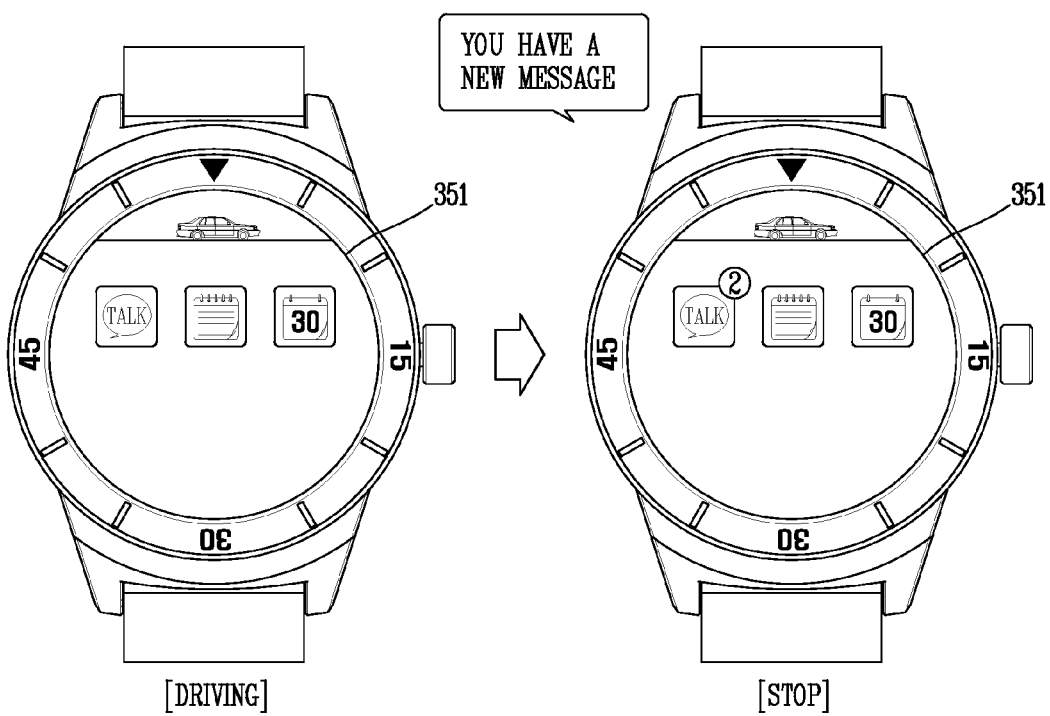

For example, as illustrated in FIG. 11, when a message is received from an external terminal through a network, the controller 180 may not output notification information notifying the reception of the message when the driving speed of the vehicle is over a preset speed (e.g., in a state that the driving speed of the vehicle is not 0).

When the driving speed of the vehicle is lower than the preset speed, the controller 180 may simultaneously output every notification information notifying events which were generated while the output of the notification information was restricted.

For example, as illustrated in FIG. 11, when the driving speed of the vehicle is lower than the preset speed (e.g., in the state that the driving speed of the vehicle is not 0), the controller 180 may output the notification information notifying the message reception. In this instance, the controller 180 may output every notification information which was generated while the output of the notification information was restricted.

When the driving speed of the vehicle is more than the preset speed, the controller 180 may output notification information relating to an event meeting a preset condition. The preset condition may be a condition that a message including a specific word should be received, a condition that a message or a call should be received from a specific external terminal, and the like.

For example, when a message or a call signal is received from a specific external terminal, the controller 180 may output notification information related to the message or the call signal. The specific external terminal may be an external terminal which has been set as a favorite by the user. The favorites may be settings for the user to quickly search for external terminals corresponding to frequently-used contact numbers.

That is, the present invention may reduce driver's distraction, which is caused due to notification information provided during the driver's driving. In addition, the present invention may allow the user to receive notification information related to an important event even while the user is driving a vehicle.

When the driving mode is executed, the controller 180 may execute a drowsiness prediction function of predicting drowsiness based on driver's biometric data and measurement of carbon dioxide density (concentration or level) within a vehicle, and providing warning information. The function may also be called various names, such as a drowsiness warning function, a safe driving aid function and the like, as well as the drowsiness prediction function.

In more detail, when the driving mode is executed, the controller 180 may activate a carbon dioxide measurement sensor for measuring of the density or level of carbon dioxide within a vehicle. Also, the controller 180 may calculate drowsiness on the basis of information related to a driver's heart rate and the carbon dioxide density.

The drowsiness may have a greater value when the driver's heart rate is lower and the carbon dioxide density is higher. For example, the drowsiness may be calculated on the basis of the current heart rate of the driver and current carbon dioxide density, as compared with a reference heart rate and a reference carbon dioxide density.

The controller 180 may also determine driving safety based on the drowsiness. For example, the controller 180 may determine lower driving safety when high drowsiness is calculated.

Figure 12A:
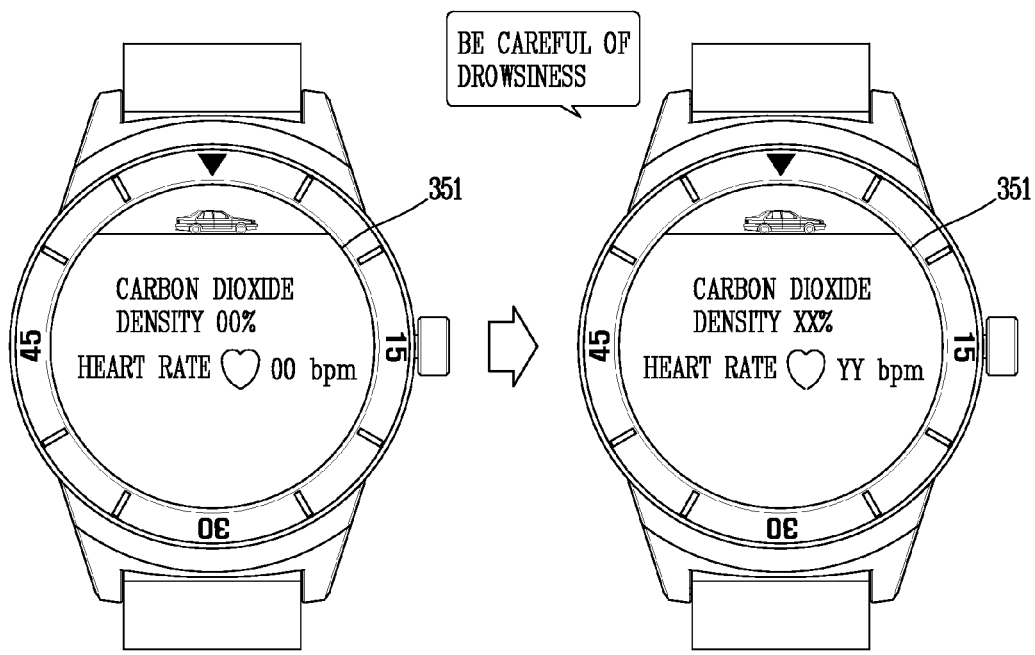

When the driving safety is less than a preset value, the controller 180 may output warning information. The warning information may be output in at least one of visual, audible and tactile manners. For example, as illustrated in FIG. 12A, when the driving safety is less than the preset value, the controller 180 may audibly output warning information, such as "Be careful of drowsiness."

In such a manner, the present invention can improve driving safety by accurately recognizing the user's biometric data using the characteristic of the watch type terminal worn on the user's wrist, determining driving safety based on the recognized biometric data, and providing warning information related to the driving safety to the user.

Figure 12B:
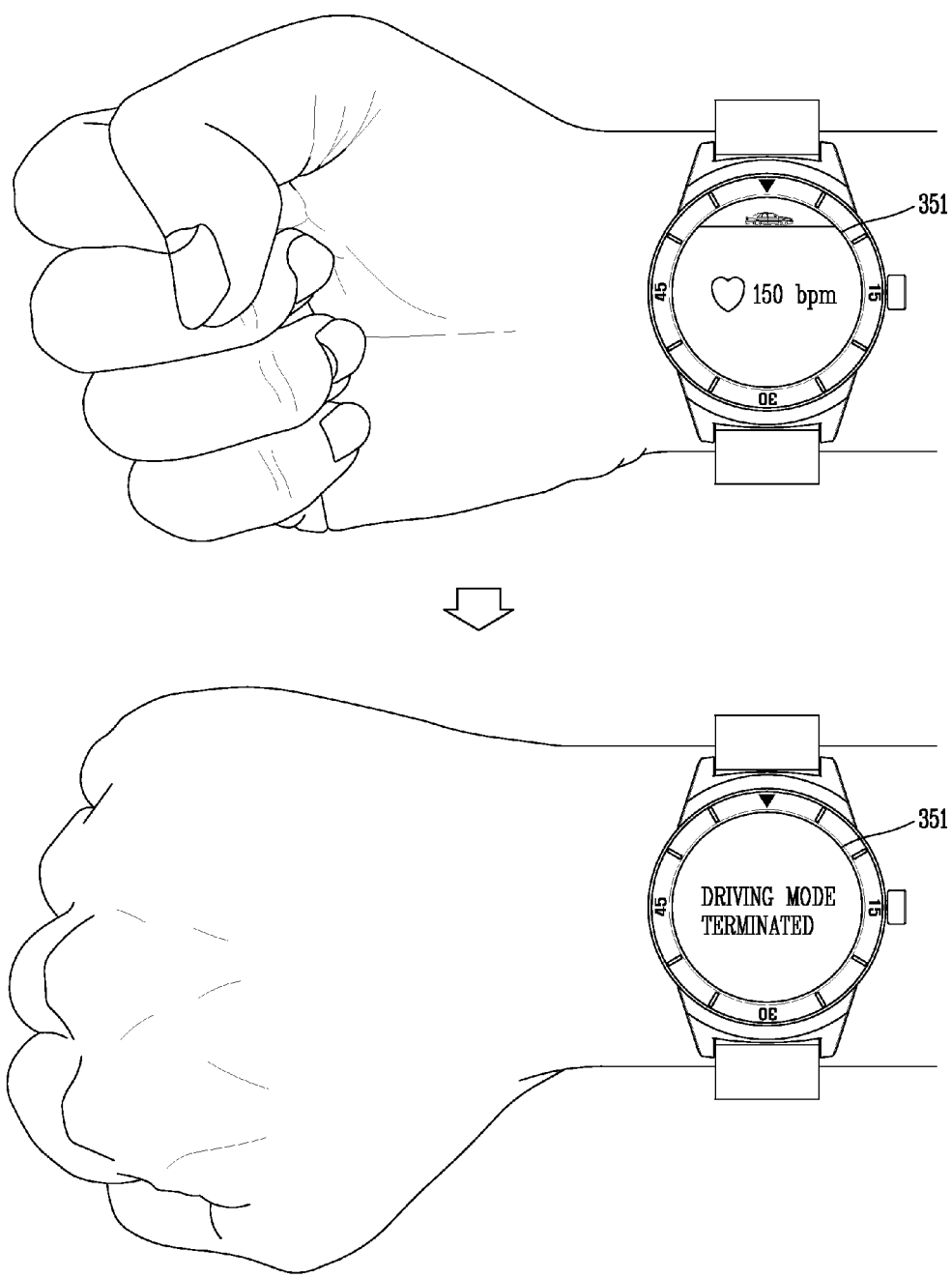

Meanwhile, the present invention may terminate the drowsiness prediction function when the sensing strength of the user's biometric data is lower than a preset strength level. For example, as illustrated in FIG. 12B, the user may rotate the watch type terminal from inner to outer sides of a wrist. In this instance, as the watch type terminal is located at the outer side of the wrist, the controller 180 may terminate the drowsiness prediction function when the sensing strength of the user's biometric data is lower than the preset strength level.

The foregoing description has been given of the method of executing the driving mode through the watch type terminal. This may allow for providing various functions associated with driving of a vehicle through the watch type terminal.

Hereinafter, a method of executing a driving mode through the watch type terminal will be described. FIG. 3A to 14b are conceptual views illustrating a method of executing an exercise mode.

The watch type terminal disclosed herein may execute an exercise mode when the sensing strength of the user's biometric data is more than a preset strength level and a motion of the watch type terminal corresponds to a preset motion. For example, when the sensing strength of the user's biometric data is more than the preset strength level and the motion of the watch type terminal corresponds to a rotary motion having a second direction (e.g., a counterclockwise direction when the watch type terminal is worn on a right wrist), the controller 180 may execute the exercise mode. As another example, when the sensing strength of the user's biometric data is more than the preset strength level and the motion of the watch type terminal corresponds to a motion toward the user's elbow, the controller 180 may execute the exercise mode.

The exercise mode may refer to a state of a watch type terminal in which at least one of functions can be executed, and examples of the functions may include a function of measuring a user's motion using at least one sensor provided in the watch type terminal and recording the measured user's motion, a function of measuring a moving distance and a position, a calorie consuming function according the user's motion, a media file reproducing function and an exercise recommending function. The at least one function may be functions included in one application, or functions executed through different applications.

Meanwhile, when the user's motion meets a preset condition, the controller 180 of the watch type terminal may output guide information for an execution of the exercise mode. The user's motion may be determined based on a motion of the watch type terminal. Here, the guide information may be output when the sensing strength of the user's biometric data is lower than a preset strength level.

The preset condition may be preset by a user, preset when the watch type terminal is presented on the market, or set by an exercise application installed in the water type terminal.

Figure 13A:
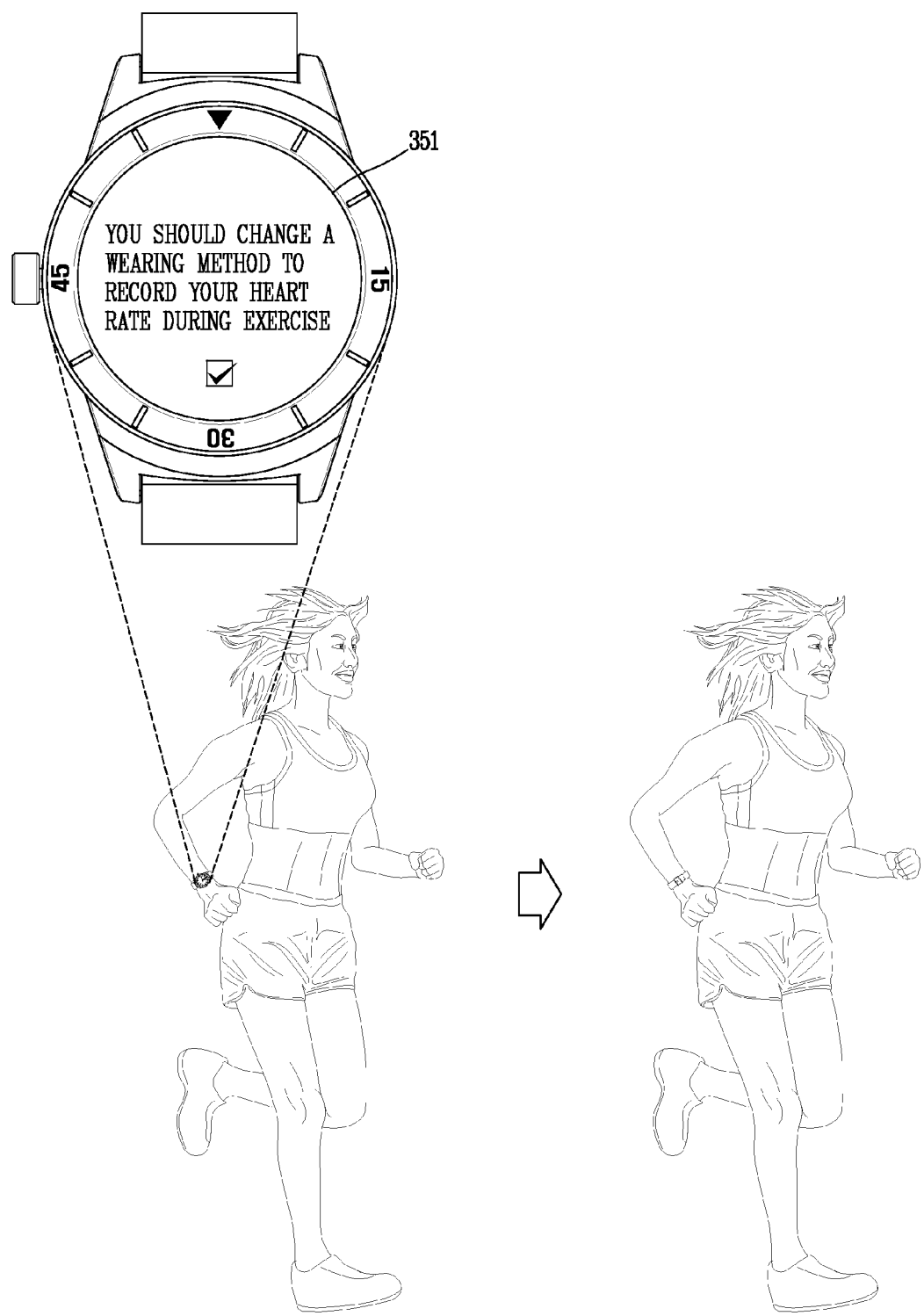
FIGS. 13A, 13B, 14A and 14B are conceptual views illustrating a method of executing (or activating) an exercise mode in a watch type terminal.
Figure 13B:
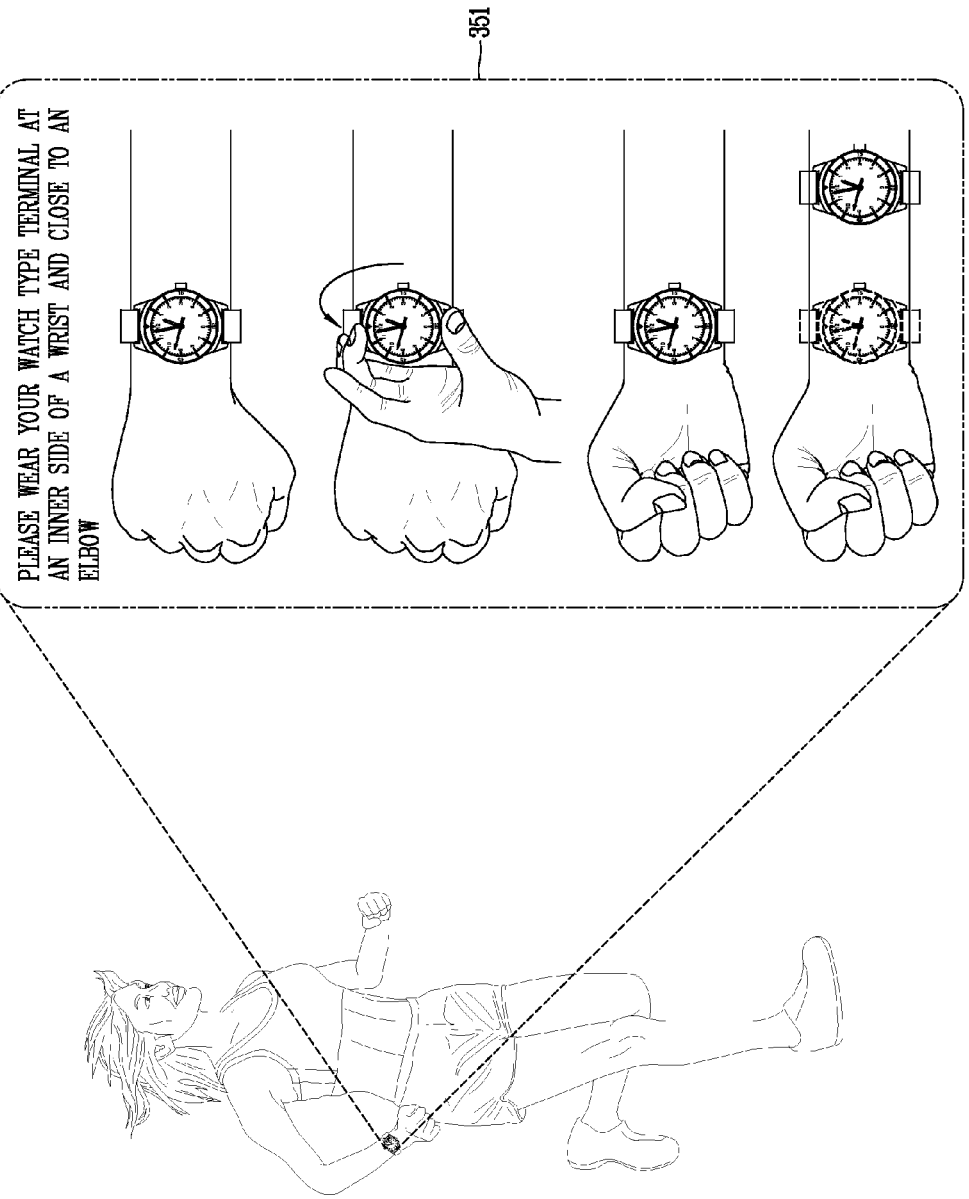

The guide information may be information for guiding a change of a position where the watch type terminal is proximate to or comes in contact with a human body such that the sensing strength of the user's biometric data can increase to accurately sense the user's motion. For example, as illustrated in FIG. 13A, the controller 180 may output guide information, such as "You should change a wearing method to record your heart rate during exercise," on the display unit 351. Also, as illustrated in FIG. 13B, the guide information may further include wearing method information, such as "Please wear your watch type terminal at an inner side of a wrist or close to an elbow.

Also, the guide information may be output in at least one of visual, audible and tactile manners. For example, the controller 180 may provide guide information through vibration when the user's motion meets a preset condition.

The guide information may not be output even though the user's motion meets the preset condition, when the sensing strength of the user's biometric data is more than a preset strength level.

The controller 180 may stop the output of the guide information when the exercise mode is executed.

When the exercise mode is executed, the controller 180 may activate at least one sensor associated with the exercise mode to accurately measure the user's motion.

The at least one sensor may be a sensor, such as an acceleration sensor, a gyro sensor, a location detection sensor (e.g., GPS sensor), and the like, each for sensing a user's motion. The activation of the at least one sensor may refer to supplying current to the at least one sensor such that motion information can be received through the at least one sensor.

Also, the controller 180 may store the motion information measured by the at least one sensor in the memory 170. In addition, the controller 180 may generate exercise record information or calculate consumed calories based on the motion information measured by the at least one sensor.

The exercise record information may be information in which the user's motion information is recorded on the basis of time, day, month and year. Also, the exercise record information may be record information in which motion information received from an external terminal belonging to another user which has previously been authenticated is compared with motion information on the user having the watch type terminal. For example, the exercise record information may be ranking information that numerical values of motion information related to another user and motion information related to the user of the watch type terminal are compared with each other.

When the exercise mode is executed, the controller 180 may identify the user on the basis of the user's biometric data. That is, the controller 180 may utilize the user's biometric data as the user's identification information.

In this instance, the controller 180 may reproduce a media file, which is associated with the user's biometric data on the basis of the user's biometric data. That is, the present invention can identify a user by using the user's biometric data so as to provide a media file suitable for the identified user.

The media file may include a music file and a video file. The media file may be set directly by the user or set according to a usage pattern of the identified user. The usage pattern may include information related to a number of reproduction of the media file, a genre of the media file, a reproduction time of the media file, and the like. For example, the media file may be a media file which is frequently reproduced by the identified user.

Figure 14A:
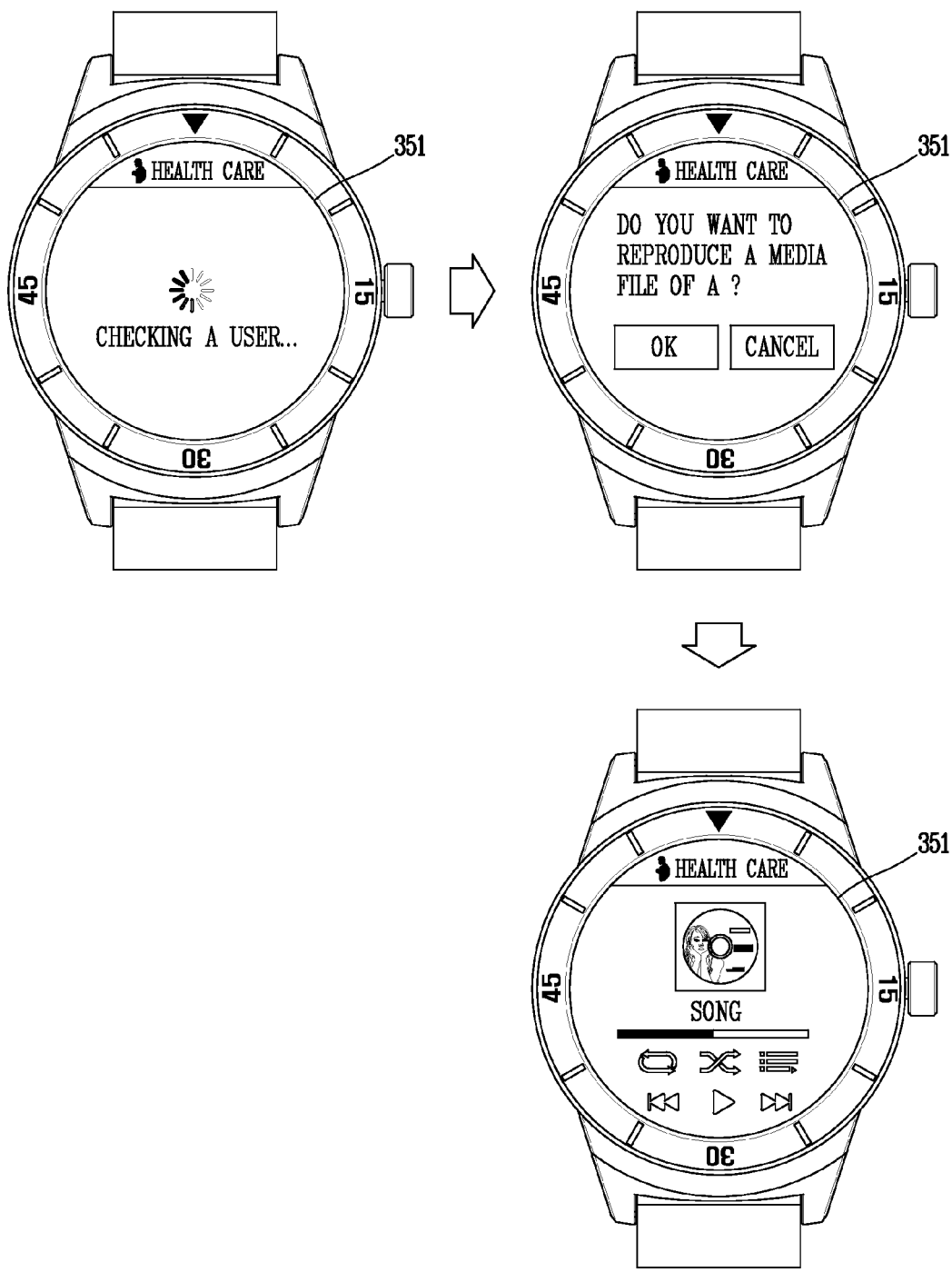

When the exercise mode is executed, if the user is identified based on the user's biometric data, the controller 180 may output information regarding the identified user on the display unit 180. For example, as illustrated in FIG. 14A, when a user "A" is identified based on the user's biometric data, the controller 180 may output notification information, such as "Do you want to reproduce a media file of A?," on the display unit 351.

In addition, the controller 180 may provide an exercise method or program based on the user's biometric data. In this case, the controller 180 may provide an appropriate exercise method or program on the basis of previous exercise record information, health information and the like in relation to the identified user. The exercise record information may include information relating to an average amount of exercise, preferred exercise type information and the like regarding the user. Also, the health information may include height, weight and hospital record of the user.

Figure 14B:
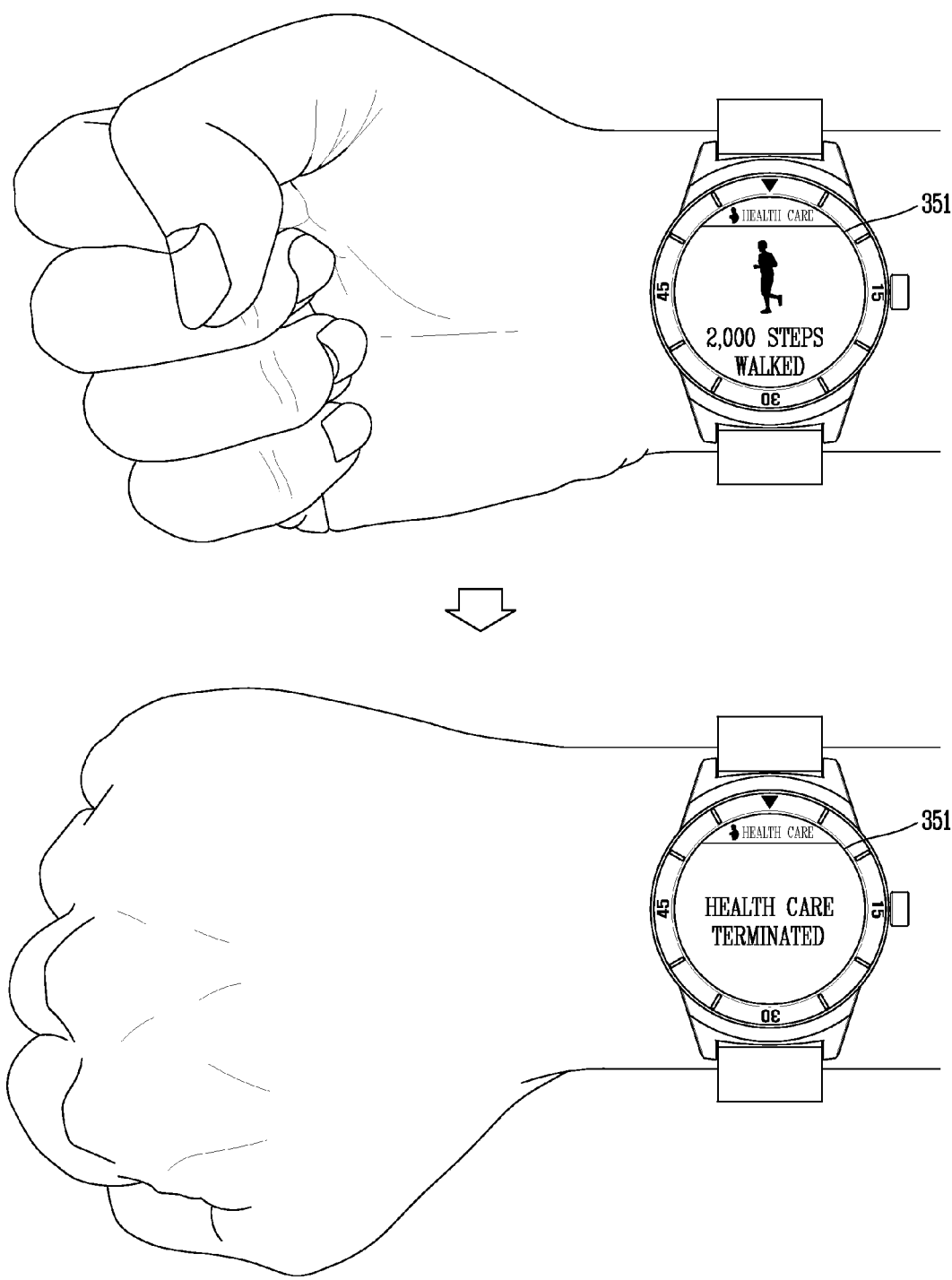

Meanwhile, while the exercise mode is executed, when it is sensed the sensing strength of the user's biometric data is lower than a preset strength level, the controller 180 may output guide information for increasing the sensing strength of the user's biometric data. The guide information may include information relating to a proximate or contact position of the watch type terminal with respect to the user's body. After the output of the guide information, when the sensing strength of the user's biometric data sensed has increased more than the preset strength level again, the controller 180 may terminate the output of the guide information. On the other hand, as illustrated in FIG. 14B, after the output of the guide information, when the sensing strength of the user's biometric data sensed is decreased lower than the preset strength level again, the controller 180 may terminate the executed exercise mode. The termination of the exercise mode may refer to deleting functions associated with the exercise mode from a RAM of the watch type terminal such that the exercise mode is not executed any more.

Also, the controller 180 may temporarily stop the executed exercise mode as soon as outputting the guide information. The temporary stop of the executed exercise mode may refer to restricting only an execution of functions included in the exercise mode while executing the exercise mode. Even in this instance, similar to the aforementioned, the controller 180 may release the temporary stop of the exercise mode or terminate the executed exercise mode according to the sensing strength of the user's biometric data sensed within a preset time after the output of the guide information.

The controller 180 may also immediately terminate the exercise mode, without the output of the guide information, when the sensing strength of the user's biometric data is less than the preset strength level.

The foregoing description has been given of the method of executing the exercise mode in the watch type terminal. This may allow for more accurate measurement and record of the user's biometric data upon execution of the exercise mode.

Figure 15A:
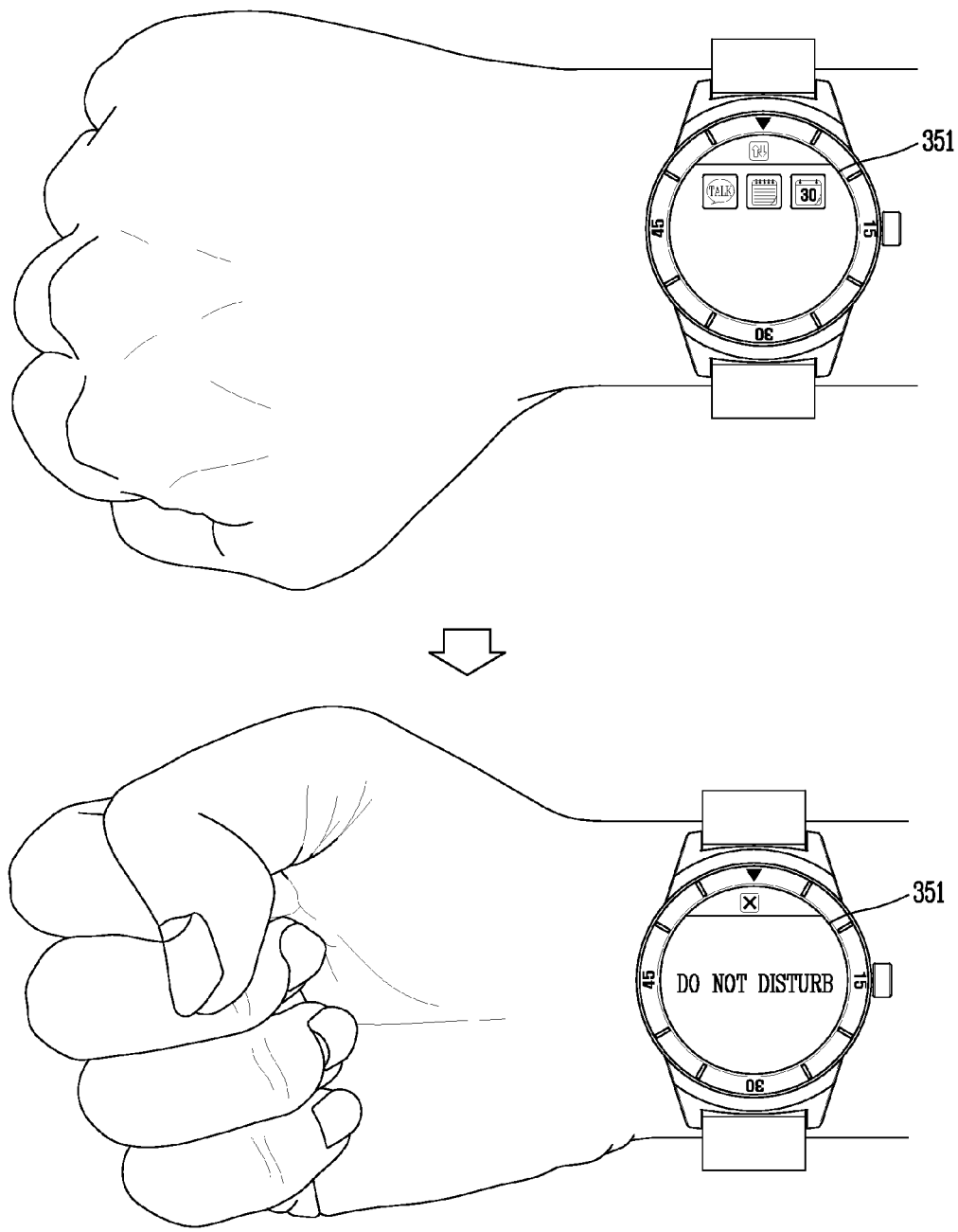
FIGS. 15A and 15B are conceptual views illustrating a method of executing a study mode in a watch type terminal.
Figure 15B:
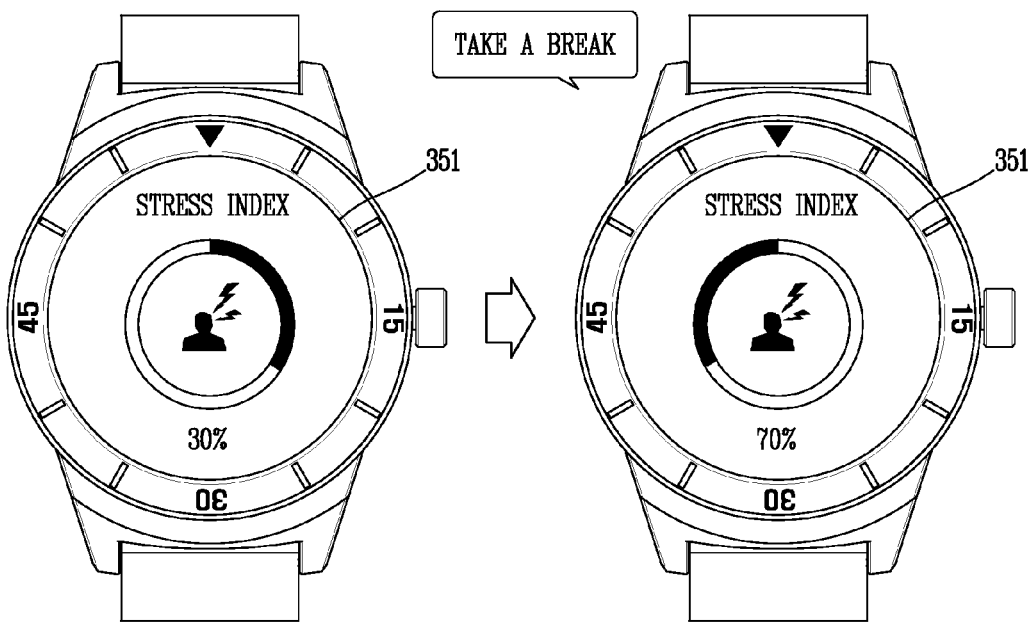

Hereinafter, a method of executing a study mode in the watch type terminal will be described. FIGS. 15A and 15B are conceptual views illustrating a method of executing a study mode in a watch type terminal.

The controller 180 of the watch type terminal may execute a study mode when the sensing strength of the user's biometric data is more than a preset strength level and the motion of the watch type terminal corresponds to a preset motion. For example, when the sensing strength of the user's biometric data is more than the preset strength level and the motion of the watch type terminal is a rotary motion in a first direction (e.g., a clockwise direction when the watch type terminal is worn on a right wrist), the controller 180 may execute a study mode.

The study mode may refer to a state of a watch type terminal in which at least one function is executed, and examples of the at least one function may include a function of restricting an output of notification information, a function of restricting data communication through a network, a function of measuring a stress index and a stopwatch function.

The study mode may also be set to be executed in a specific time section (or time zone). Under a state that a current time belongs to a specific time section, when the sensing strength of the user's biometric data is lower than the preset strength level, the controller 180 may output guide information for the user to move the watch type terminal.

The guide information may be output in at least one of visual, audible and tactile manners.

The guide information may be information which indicates a moving direction of the watch type terminal such that the watch type terminal can be located proximate to or come in contact with a specific position of the user's body. For example, the guide information may include information, such as "Please move the watch type terminal to the inner side of a wrist or toward an elbow to execute the study mode."

Also, the guide information may not be output any more when the sensing strength of the user's biometric data is more than the preset strength level. The guide information may not be output any more when the study mode is executed.

When the study mode is activated, the controller 180 may execute a function of restricting an output of notification information. The function of restricting the output of the notification information may be a function of restricting in the study mode an output of notification information relating to an event, which is generated from at least one of a plurality of applications installed in the watch type terminal. The event may be a message reception event, a call signal generation event, an update event, a schedule notice event and the like. In this instance, the notification information may be output at once when the study mode executed is deactivated.

The controller 180 may also execute a function of restricting data communication through a network. The function of restricting the data communication through the network may refer to a function of deactivating at least one wireless communication module (e.g., an LTE communication module, a Bluetooth module, a WiFi module, etc.) provided in the watch type terminal, such that the data communication cannot be executed. For example, as illustrated in FIG. 15A, when the study mode is executed, the controller 180 may deactivate the LTE communication module.

The controller 180 may execute a function of measuring a stress index. The function of measuring the stress index may refer to a function of measuring the stress index by measuring the user's heart rate. In more detail, the controller 180 may determine a higher stress index when the heart rate increases.

When the stress index is more than a preset value, the controller 180 may output warning information related to the stress index. For example, as illustrated in FIG. 15B, when the stress index is more than the preset value, the controller 180 may output notification information, such as "Take a break," by voice.

When the study mode is executed, the controller 180 may execute a stopwatch function. The stopwatch function may refer to a function of controlling start and end of time measurement according to a sensing strength of the user's biometric data. The controller 180 may start the time measurement when the sensing strength of the user's biometric data is a first strength level, while ending the time measurement when the sensing strength of the user's biometric data is a second strength level, lower than the first strength level.

The foregoing description has been given of the method of executing the study mode. This may allow for determining the stress index using the user's biometric data so as to provide appropriate warning information.

Hereinafter, a method of executing a payment mode in a watch type terminal will be described. FIGS. 16A to 16D are conceptual views illustrating a method of executing a payment mode in a watch type terminal.

The watch type terminal disclosed herein may execute a payment mode when the sensing strength of the user's biometric data is more than a preset strength level and the motion of the watch type terminal corresponds to a preset motion. For example, when the sensing strength of the user's biometric data is more than the preset strength level and the motion of the watch type terminal is a rotary motion in a first direction (e.g., a clockwise direction when the watch type terminal is worn on a right wrist), the controller 180 may execute the payment mode.

That is, the controller 180 may execute the payment mode when the sensing strength of the user's biometric data increases more than the preset strength level as the user rotates (or in response to the user rotating) the watch type terminal from outer to inner sides of the wrist.

The payment mode may refer to a state of a watch type terminal in which a function of activating or deactivating a payment module provided in the watch type terminal, a function of performing payment and the like are executable.

The controller 180 may first execute a function of activating or deactivating a payment module provided in the watch type terminal when the payment mode is executed.

Meanwhile, payment methods using the watch type terminal may include an NFC-based payment method and a magnetic secure transmission (MST)-based payment method. The NFC-based payment method may be implemented in the same manner as the aforementioned case where the NFC is used in a card mode. The MST-based payment method may be a method that a method of performing payment using magnetic information in a magnetic card is implemented in an electronic manner.

In more detail, according to the MST-based method, the magnetic information may be stored in a terminal, and then transmitted to a point of sales (POS) in the form of a wireless signal using a magnetic field, thereby performing the payment. That is, the watch type terminal may perform the payment through the transmission of the wireless signal without a direct contact with the POS, as conventionally done using the magnetic card.

The POS is a terminal of collecting sales information, and may refer to a terminal of performing various functions associated with a payment, such as a product management, an inventory management, an automatic credit determination and the like. The POS may be replaced with other terms, such as a payment terminal, a credit card reader, and the like.

For the use of the MST-based method, the watch type terminal may pre-store card information, security information and the like in the memory. Here, the card information may be at least one of an identification number of the conventional magnetic card, a valid date, a security number, a card provider information, and card magnetic information. Also, the security information may be the same security information as security information, which is used when the NFC module is operated in the card mode.

The watch type terminal may modulate or demodulate the magnetic field such that the stored card information and security information can be included in the magnetic field. Here, the modulation of the magnetic field may refer to changing at least one of amplitude, phase and frequency of the magnetic field. Also, the demodulation of the magnetic field may refer to generating a magnetic field before modulated by re-changing at least one of amplitude, phase and frequency of the modulated magnetic field. The watch type terminal may generate a wireless signal including the stored card information and security information, through the modulation and demodulation of the magnetic field.

When the wireless signal is generated, the watch type terminal may perform payment by transmitting the wireless signal to the POS.

Meanwhile, for security, the watch type terminal using the MST-based method may perform the payment in a manner of generating virtual card information on the basis of the card information to prevent the card information from being stored in the POS, and transmitting the virtual card information to the POS. That is, the watch type terminal may reinforce security to prevent exposure of card information to the POS, in a manner of newly generating virtual card information every time of performing payment and transmitting the generated virtual card information to the POS. Also, the virtual card information may allow for reinforcing the security through a network authentication or an additional security procedure, such as finger scan, etc.

Here, when the payment mode is executed, the controller 180 may activate at least one payment module provided in the watch type terminal. The payment module may be a module of transmitting payment information to an external device (e.g., POS) which performs a payment authorization (acceptance or approval) function for performing the payment. For example, the payment module may be an NFC module compliant with the NFC-based method, an MST module compliant with the MST-based method.

That is, the present invention may perform the payment by activating the NFC module or MST module only when the sensing strength of the user's biometric data is more than a preset strength level.

Meanwhile, when the sensing strength of the user's biometric data is lower than the preset strength level, the controller 180 may keep the payment module deactivated, or may not output payment-related information on the display unit 351. In this instance, the controller 180 may not perform the payment even though receiving the user's request for the payment.

The controller 180 may also output guide information when the payment request is received while the sensing strength of the user's biometric data is lower than the preset strength level.

The guide information may be information for guiding the user to change the position where the watch type terminal comes in contact with or is located proximate to the user's body so as to increase the sensing strength of the biometric data. For example, the guide information may be information, such as "Please rotate the watch type terminal from outer to inner sides of the wrist to perform the payment."

After the output of the guide information, when the sensing strength of the user's biometric data sensed is more than the preset strength level, the controller 180 may execute the payment mode. When the payment mode is executed, the controller 180 may not output the guide information any more.

Figure 16A:
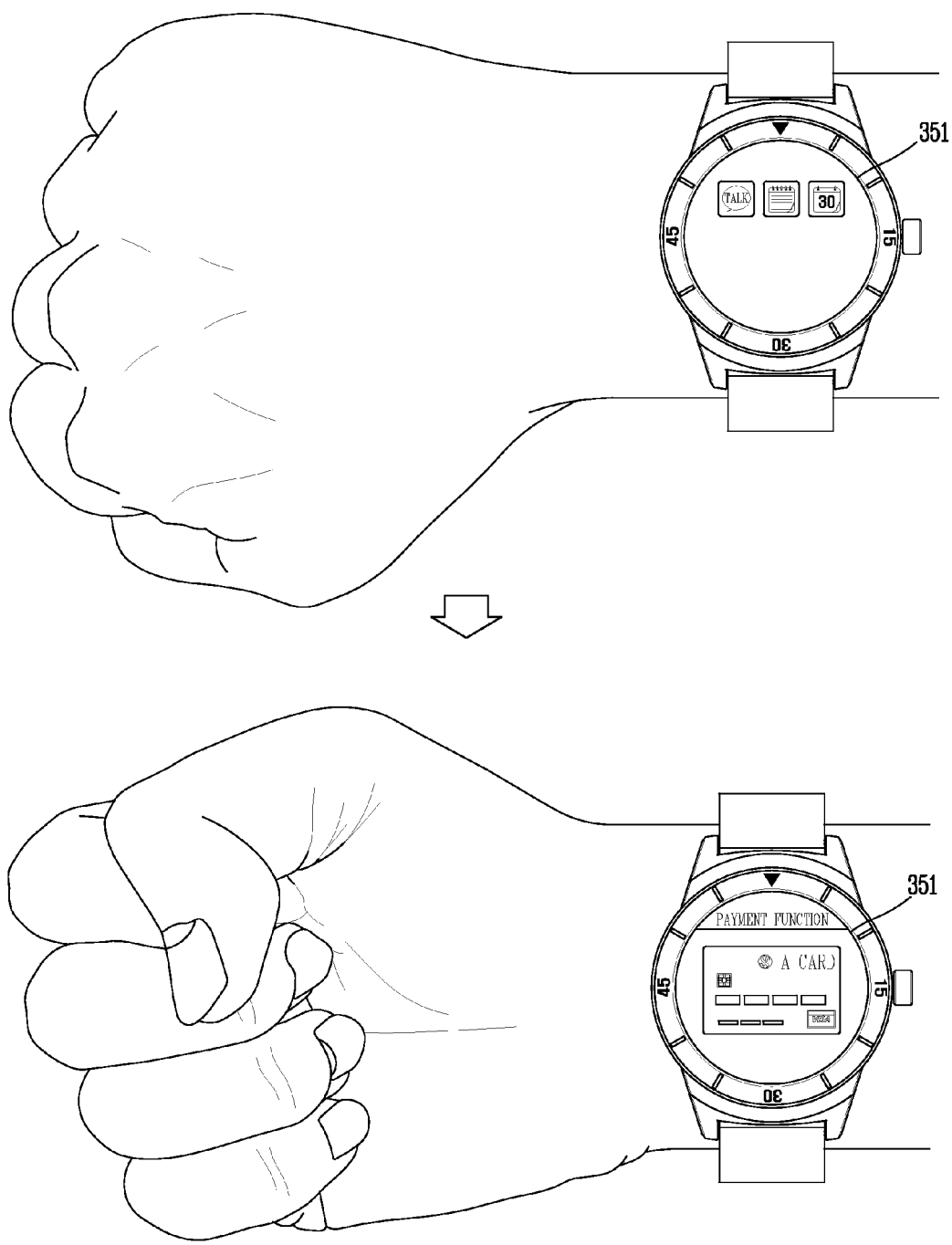
FIGS. 16A, 16B, 16C and 16D are conceptual views illustrating a method of executing a payment mode in a watch type terminal.

When the payment mode is executed, the controller 180 may output payment information on the display unit 351. For example, payment information may be output on the display unit 351 as illustrated in FIG. 16A. The payment information may include information related to payment-allowable countries, payment amount limit information, card number information, card-available period information, card company information and the like.

Figure 16B:
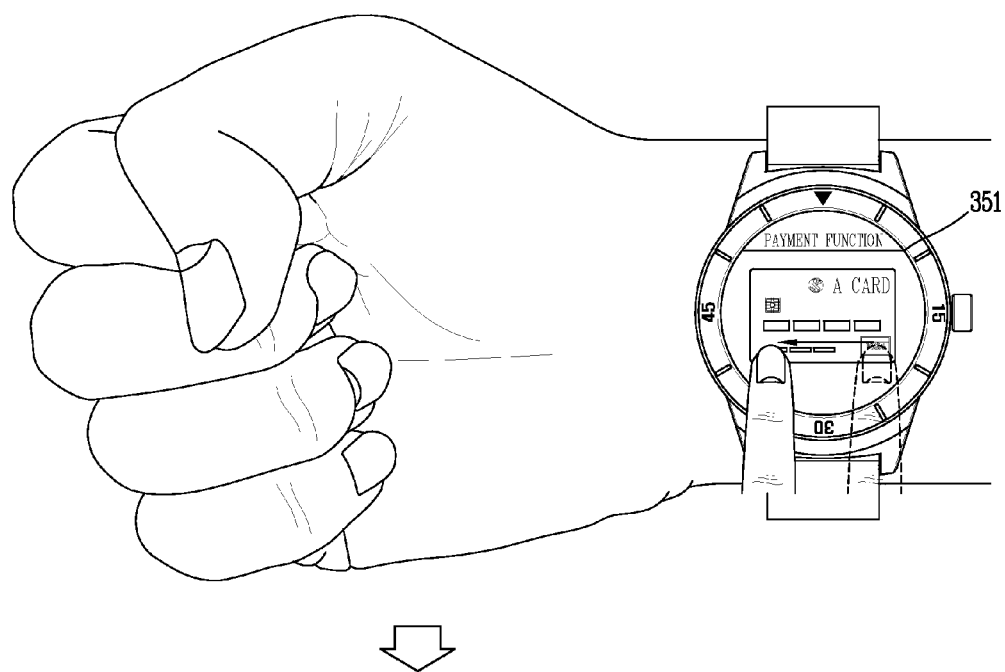
Figure 16B:
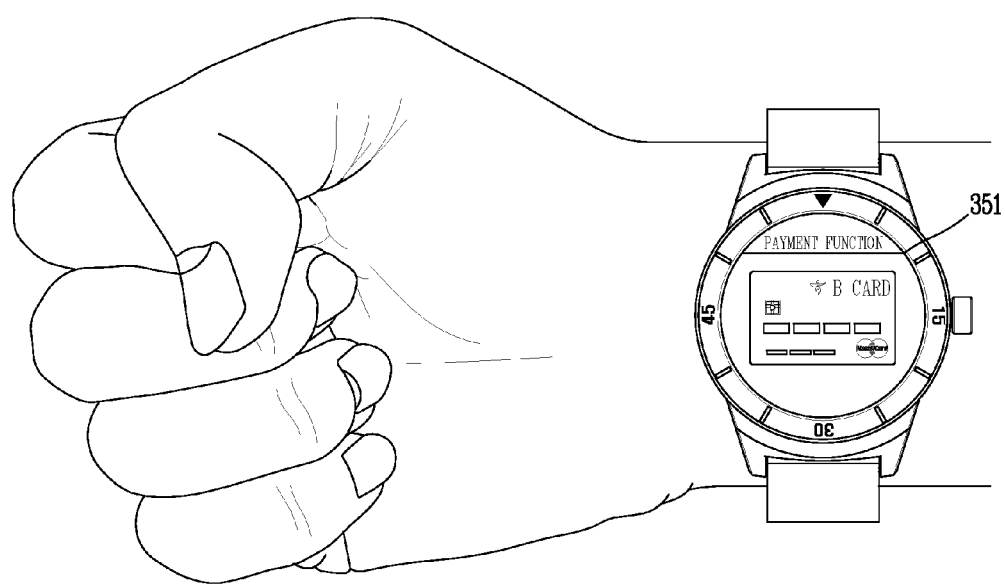

The controller 180 may change the payment information when a preset touch is applied to the payment information. For example, as illustrated in FIG. 16B, the controller 180 may change the payment information into another payment information, in response to a drag input applied to the payment information. The another payment information may include information relating to another card number, and the like.

When the payment function is executed, the controller 180 may change the payment amount limit information based on the sensing strength of the user's biometric data. In more detail, the controller 180 may more increase the payment amount limit when a higher sensing strength of the user's biometric data is sensed.

For example, the controller 180 may set the payment amount limit to a first amount of money when the sensing strength of the user's biometric data is a first strength level, while setting it to a second amount of money which is greater than the first amount of money when the sensing strength of the user's biometric data is a second strength level higher than the first strength level.

Also, the controller 180 may transmit payment information to the POS through the payment module, in response to a user's request. Also, the controller 180 may receive payment approval information or payment rejection information from the POS, in response to the payment information.

When the payment approval information is received, the controller 180 may output receipt information indicating the successful payment on the display unit 351.

Figure 16C:
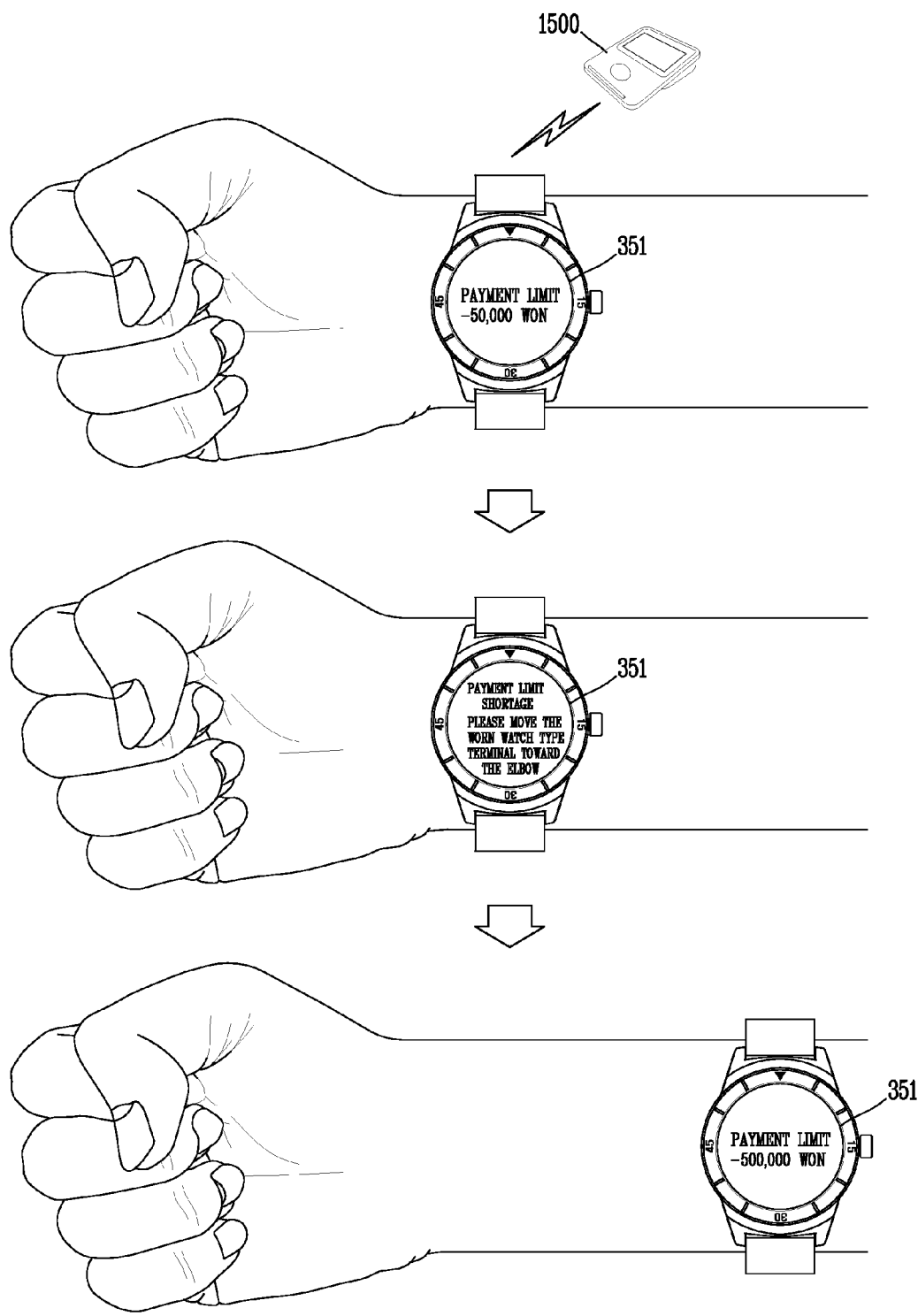

When the payment rejection information is received, the controller 180 may output a payment rejection reason, which is included in the payment rejection information, on the display unit 351. The payment rejection reason may include a payment limit shortage, invalid card information, and the like. For example, as illustrated in FIG. 16C, the controller 180 may output the payment rejection reason, such as "Payment limit shortage."

Meanwhile, when the payment rejection reason is the payment limit shortage, the controller 180 may output guide information for increasing the payment limit on the display unit 351.

The guide information may information for guiding the user to move the watch type terminal toward the elbow so as to increase the sensing strength of the user's biometric data in association with the increase in the payment amount limit. For example, as illustrated in FIG. 16C, the controller 180 may provide guide information, such as "Please move the worn watch type terminal toward the elbow," on the display unit 351.

The controller 180 may increase the payment amount limit based on the sensing strength of the user's biometric data after the output of the guide information. For example, as illustrated in FIG. 16C, the controller 180 may increase the payment amount limit information from 50,000 Won (KRW) to 500,000 Won.

Figure 16D:
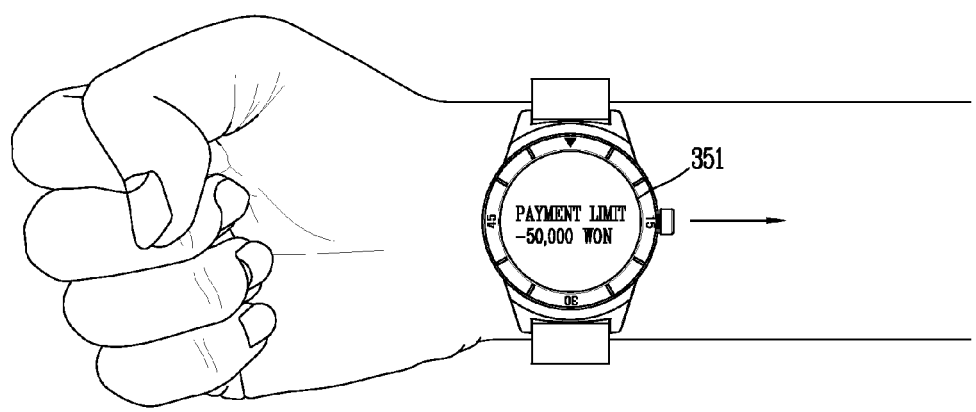
Figure 16D:
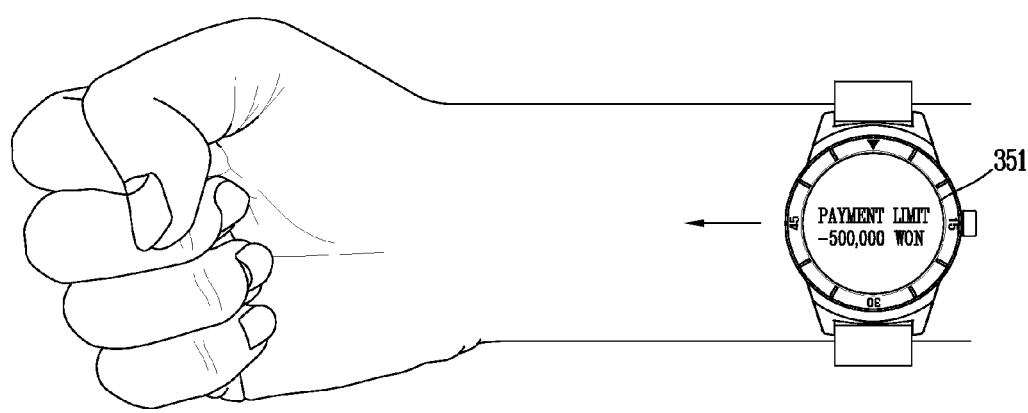
Figure 16D:
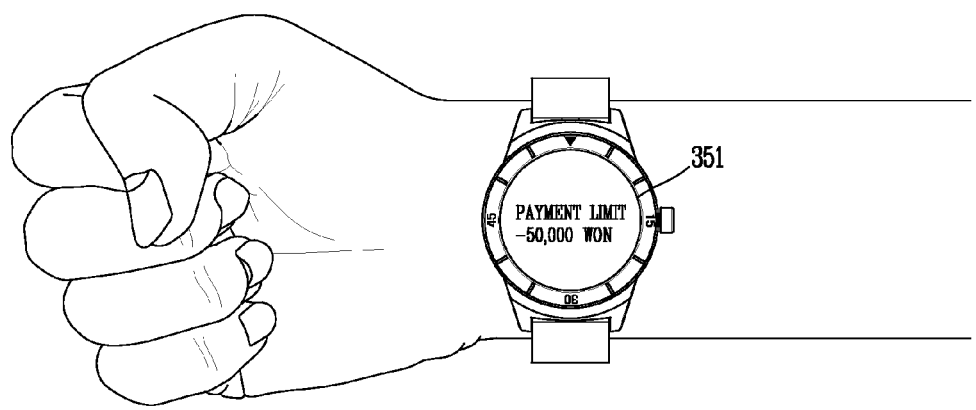

The controller 1890 may also decrease the payment amount limit based on the sensing strength of the user's biometric data. For example, as illustrated in FIG. 16D, the controller 180 may decrease the payment amount limit information to 50,000 Won when the sensing strength of the user's biometric data is lowered while the payment amount limit is set to 500,000 Won.

Meanwhile, while the payment mode is executed, when the sensing strength of the user's biometric data sensed is lower than the preset strength level, the controller 180 may output guide information. The guide information may be information indicating the weakness of the sensing strength of the user's biometric data, and information for changing a posture of the watch type terminal to increase the sensing strength of the user's biometric data. For example, the guide information may be information, such as "Please wear the watch type terminal at the inner side of the wrist or toward the elbow."

After the output of the guide information, when the sensing strength of the user's biometric data sensed is more than the preset strength level again, the controller 180 may stop the guide information and keep executing the payment mode.

On the other hand, after the output of the guide information, when the sensing strength of the user's biometric data sensed is lower than the preset strength level for a preset time, the controller 180 may deactivate the executed payment mode.

Also, the controller 180 may temporarily stop the executed payment mode as soon as outputting the guide information. In this case, after the output of the guide information, when the sensing strength of the user's biometric data sensed has increased more than the preset strength level again, the controller 180 may terminate the output of the guide information, release the temporary stop of the payment mode, and keep executing the payment mode.

On the other hand, after the output of the guide information, when the sensing strength of the user's biometric data sensed is lower than the preset strength level for a preset time, the controller 180 may deactivate the executed payment mode.

Also, when the sensing strength of the user's biometric data sensed is lower than the preset strength level, the controller 180 may immediately terminate the executed payment mode, without the output of the guide information.

The foregoing description has been given of the method of executing the payment mode through the watch type terminal. The present invention can reinforce security, in case of executing a function requiring for high security, such as payment, by way of moving the watch type terminal toward the inner side of the user's wrist. Also, various functions associated with the payment can be executed by using the sensing strength of the user's biometric data.

The present invention may include a sensing unit that is provided on a rear surface of a display unit of a watch type terminal to sense biometric data, so as to provide various functions on the basis of strength and waveform of the biometric data which change according to relative positions of the display unit and a user's body. Accordingly, the intent of the user having the watch type terminal may be determined according to the strength of the biometric data, such that the user can be provided with functions appropriate for the intent, even without a separate user setting.

Also, the present invention may recognize the user of the watch type terminal according to the waveform of the biometric data sensed by the sensing unit, and thus conveniently provide functions requiring for user authentication, even without a separate user authentication.

The present invention can be implemented as computer-readable codes in a program-recorded medium. The computer-readable medium may include all types of recording devices each storing data readable by a computer system. Examples of such computer-readable media may include hard disk drive (HDD), solid state disk (SSD), silicon disk drive (SDD), ROM, RAM, CD-ROM, magnetic tape, floppy disk, optical data storage element and the like. Also, the computer-readable medium may also be implemented as a format of carrier wave (e.g., transmission via an Internet). The computer may include the controller 180 of the terminal. Therefore, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. A wearable terminal comprising:
   a display comprising a front side and a rear side;
   a first sensing unit configured to sense a biometric characteristic and disposed at the rear side of the display to be proximate to or contact a user's body;
   a second sensing unit configured to sense a movement of the terminal; and
   a controller configured to:
   execute a different function based on the movement of the terminal when a sensing strength of the biometric characteristic via the first sensing unit is greater than a threshold strength level; and
   set the terminal to a driving mode when the sensing strength is greater than the threshold strength level and the movement of the terminal corresponds to a preset driving movement,
   wherein the sensing strength is varied based on a portion of the user's body which the first sensing unit is proximate to or is in contact with.

2. The terminal of claim 1, wherein:
   the movement of the terminal is a rotating motion in a first direction or a second direction about an axis corresponding to the user's wrist; and
   the controller is further configured to:
   set the terminal to a first mode in which functions are executed using personal information when the rotating motion is in the first direction, and
   set the terminal to a second mode in which functions are executed without using the personal information when the rotating motion is in the second direction.

3. The terminal of claim 1, wherein the biometric characteristic includes at least a heart rate or a pulse strength of the user.

4. The terminal of claim 1, wherein the controller is further configured to:
   set the terminal to a first mode in which the display is activated or deactivated based on the movement of the terminal when the sensing strength is lower than the threshold strength level, and
   set the terminal to a second mode in which the display is not activated or deactivated based on the movement of the terminal when the sensing strength is greater than the threshold strength level.

5. The terminal of claim 4, wherein the controller is further configured to maintain the display in a deactivated state while the terminal is in the second mode.

6. The terminal of claim 4, wherein the controller is further configured to activate the display in response to a user command while the terminal is in the second mode.

7. The terminal of claim 1, wherein the controller is further configured to:
calculate a driving safety value based on a biometric data value corresponding to the biometric characteristic; and
cause an output of notification information when the driving safety value is less than a threshold value.

8. The terminal of claim 1, wherein the controller is further configured to activate at least one sensor for sensing information related to driving a vehicle when the terminal is set to the driving mode.

9. The terminal of claim 1, wherein:
the controller is further configured to restrict output of notification information while the terminal is in the driving mode; and
the notification information is generated from at least one application installed at the terminal.

10. The terminal of claim 1, wherein the controller is further configured to:
determine a user motion corresponding to the sensed movement of the terminal;
cause an output of notification information to move the second sensing unit to a specific position of the user's body when the user motion corresponds to a preset motion; and
set the terminal to an exercise mode in which at least one value of movement of the terminal is measured when the sensing strength is greater than the threshold strength level after the output of the notification information.

11. The terminal of claim 10, wherein the notification information comprises instructions to position the second sensing unit to come in contact with or be proximate to the specific position of the user's body.

12. The terminal of claim 1, wherein the controller is further configured to execute a payment function when the sensing strength is greater than the threshold strength level.

13. The terminal of claim 12, wherein the controller is further configured to set a payment limit of the payment function based on the sensing strength.

14. The terminal of claim 1, wherein the controller is further configured to set an output method of notification information when it is determined that the user is in a vehicle based on the movement of the terminal and the sensing strength is greater than the threshold strength level.

15. A method for controlling a wearable terminal, the method comprising:
sensing a biometric characteristic of a user via a first sensor;
sensing a movement of the terminal via a second sensor;
executing a different function based on the movement of the terminal when a sensing strength of the biometric characteristic via the first sensor is greater than a threshold strength level;
setting the terminal to a driving mode when the sensing strength is greater than the threshold strength level and the movement of the terminal corresponds to a preset driving movement,
wherein the sensing strength is varied based on a portion of the user's body which the terminal is proximate to or is in contact with.

16. The method of claim 15, wherein the movement of the terminal is a rotating motion in a first direction or a second direction about an axis corresponding to the user's wrist.

17. The method of claim 16, further comprising:
setting the terminal to a first mode in which functions are executed using personal information when the rotating motion is in the first direction; and
setting the terminal to a second mode in which functions are executed without using the personal information when the rotating motion is in the second direction.

18. The method of claim 15, further comprising setting an output method of notification information when it is determined that the user is in a vehicle based on the movement of the terminal and the sensing strength is greater than the threshold strength level.

19. The method of claim 15, further comprising:
setting the terminal to a first mode in which a display of the terminal is activated or deactivated based on the movement of the terminal when the sensing strength is lower than the threshold strength level, and
setting the terminal to a second mode in which the display is not activated or deactivated based on the movement of the terminal when the sensing strength is greater than the threshold strength level.

* * * * *